US007531548B2

(12) United States Patent
Guillemont et al.

(10) Patent No.: US 7,531,548 B2
(45) Date of Patent: May 12, 2009

(54) HIV INHIBITING 5-CARBO- OR HETEROCYCLIC SUBSTITUTED PYRIMIDINES

(75) Inventors: Jerôme Emile Georges Guillemont, Andé (FR); Jan Heeres, Vosselaar (BE); Paulus Joannes Lewi, Turnhout (BE)

(73) Assignee: Tibotec Pharmaceuticals Ltd, County Cork (IE)

( * ) Notice: Subject to any disclaimer, the term of this patent is extended or adjusted under 35 U.S.C. 154(b) by 0 days.

(21) Appl. No.: 11/576,068

(22) PCT Filed: Sep. 29, 2005

(86) PCT No.: PCT/EP2005/054931

§ 371 (c)(1),
(2), (4) Date: Mar. 27, 2007

(87) PCT Pub. No.: WO2006/035068

PCT Pub. Date: Apr. 6, 2006

(65) Prior Publication Data

US 2007/0208022 A1 Sep. 6, 2007

(30) Foreign Application Priority Data

Sep. 30, 2004 (EP) .................. 04104814

(51) Int. Cl.
C07D 239/48 (2006.01)
C07D 239/50 (2006.01)
C07D 239/34 (2006.01)
C07D 239/38 (2006.01)
C07D 239/42 (2006.01)
C07D 401/12 (2006.01)
C07D 403/12 (2006.01)
C07D 405/12 (2006.01)
C07D 409/12 (2006.01)
C07D 413/12 (2006.01)
A61K 31/505 (2006.01)
A61P 31/18 (2006.01)

(52) U.S. Cl. ............ 514/272; 514/275; 544/321; 544/324; 544/325

(58) Field of Classification Search ............ 544/321, 544/324, 325; 514/272, 275
See application file for complete search history.

(56) References Cited

U.S. PATENT DOCUMENTS 6,197,779 B1 * 3/2001 Andries et al. ............ 514/272

6,593,326 B1 7/2003 Bradbury et al.
2003/0036543 A1 2/2003 Bebbington et al.

FOREIGN PATENT DOCUMENTS

| WO | WO 91/18887 A1 | 12/1991 |
|---|---|---|
| WO | WO 99/50250 A1 | 10/1999 |
| WO | WO 00/27825 A1 | 5/2000 |

OTHER PUBLICATIONS

International Search Report dated Jun. 20, 2006 for related International Application No. PCT/EP2005/054931.

* cited by examiner

Primary Examiner—Venkataraman Balasubramanian
(74) Attorney, Agent, or Firm—Laura A. Donnelly

(57) ABSTRACT

HIV replication inhibitors of formula (I) N-oxides, a pharmaceutically acceptable addition salts, a quaternary amines or a stereoisomeric forms thereof, wherein -$a^1$=$a^2$-$a^3$=$a^4$- is —CH=CH—CH=CH—, —N=CH—CH=CH—, —N=CH—N=CH—, —N=CH—CH=N—, —N=N—CH=CH—; -$b^1$=$b^2$-$b^3$=$b^4$- is —CH=CH—CH=CH—, —N=CH—CH=CH—, —N=CH—N=CH—, —N=CH—CH=N—, —N=N—CH=CH—; $R^1$ is hydrogen; aryl; formyl; $C_{1-6}$alkylcarbonyl; optionally substituted $C_{1-6}$alkyl; $C_{1-6}$alkyloxycarbonyl; $R^2$ is OH; halo; optionally substituted $C_{1-6}$alkyl, $C_{2-6}$alkenyl or $C_{2-6}$alkynyl; substituted carbonyl; carboxyl; CN; nitro; amino; substituted amino; polyhalomethyl; polyhalomethylthio; —S(=O)r$R^6$; C(=NH)$R^6$; $R^{2a}$ is CN; amino; substituted amino; optionally substituted $C_{1-6}$alkyl; halo; optionally substituted $C_{2-6}$alkyloxy; substituted carbonyl; —CH=N—NH—C(=O)—$R^{16}$; optionally substituted $C_{1-6}$alkyloxy $C_{1-6}$alkyl; substituted $C_{2-6}$alkenyl or $C_{2-6}$alkynyl; —C(=N—O—$R^8$)—$C_{1-4}$alkyl; $R^7$ or —$X_3$—$R^7$; $X_1$ is —$NR^1$—, —O—, —C(=O)—, $CH_2$, —CHOH—, —S—, —S(=O)$_r$—; $R^3$ is CN; amino; $C_{1-6}$alkyl; halo; optionally substituted $C_{1-6}$alkyloxy; substituted carbonyl; —CH=N—NH—C(=O)—$R^{16}$; substituted $C_{1-6}$alkyl; optionally substituted $C_{1-6}$alkyloxy $C_{1-6}$alkyl; substituted $C_{2-6}$alkenyl or $C_{2-6}$alkynyl; —C(=N—O—$R^8$)— $C_{1-4}$alkyl; $R^7$; —$X_3$—$R^7$; $R^4$ is halo; OH; optionally substituted $C_{1-6}$alkyl, $C_{2-6}$alkenyl or $C_{2-6}$alkynyl; $C_{3-7}$cycloalkyl; $C_{1-6}$alkyloxy; CN; nitro; polyhalo $C_{1-6}$alkyl; polyhalo $C_{1-6}$alkyloxy; substituted carbonyl; formyl; amino; mono- or di($C_{1-4}$alkyl)amino or $R^7$; $R^5$ is —Y—$C_qH2_q$-L or —$C_qH_{2q}$—Y—$C_rH_{2r}$-L; L is aryl or Het; processes for the preparation of these compounds, pharmaceutical compositions comprising these compounds as active ingredient and the use of these compounds for the prevention or the treatment of HIV infection.

18 Claims, No Drawings

HIV INHIBITING 5-CARBO- OR HETEROCYCLIC SUBSTITUTED PYRIMIDINES

CROSS REFERENCE TO RELATED APPLICATIONS

This application is a national stage application of Patent Application No. PCT/EP2005/054931, filed Sep. 29, 2005, which application claims priority from EPO Patent Application No. 04104814.1, filed Sep. 30, 2004, both of which are hereby incorporated by reference in their entirety.

The present invention is concerned with pyrimidine derivatives having HIV (Human Immunodeficiency Virus) replication inhibiting properties. The invention further relates to methods for their preparation and pharmaceutical compositions comprising them. The invention also relates to the use of said compounds in the prevention or the treatment of HIV infection.

Resistance of the HIV virus against currently available HIV drugs continues to be a major cause of therapy failure. This has led to the introduction of combination therapy of two or more anti-HIV agents usually having a different activity profile. Significant progress was made by the introduction of HAART therapy (Highly Active Anti-Retroviral Therapy), which has resulted in a significant reduction of morbidity and mortality in HIV patient populations treated therewith. HAART involves various combinations of nucleoside reverse transcriptase inhibitors (NRTIs), non-nucleoside reverse transcriptase inhibitors (NNRTIs) and protease inhibitors (PIs). Current guidelines for antiretroviral therapy recommend such triple combination therapy regimen for initial treatment. However, these multidrug therapies do not completely eliminate HIV and long-term treatment usually results in multidrug resistance. In particular, half of the patients receiving anti-HIV combination therapy do not respond fully to the treatment, mainly because of resistance of the virus to one or more drugs used. It also has been shown that resistant virus is carried over to newly infected individuals, resulting in severely limited therapy options for these drug-naive patients.

Therefore there is a continued need for new combinations of active ingredients that are effective against HIV. New types of anti-HIV effective active ingredients, differing in chemical structure and activity profile are useful in new types of combination therapy Finding such active ingredients therefore is a highly desirable goal to achieve.

The present invention is aimed at providing particular novel series of pyrimidine derivatives having HIV replication inhibiting properties. WO 99/50250, WO 00/27825 and WO 01/85700 disclose certain substituted aminopyrimidines and WO 99/50256 and EP-834 507 disclose aminotriazines having HIV replication inhibiting properties.

The compounds of the invention differ from prior art compounds in structure, pharmacological activity and/or pharmacological potency. It has been found that the introduction of carbocyclic or heterocyclic groups linked to the 5-position of specifically substituted pyrimidines results in compounds the compounds not only acting favorably in terms of their capability to inhibit the replication of Human Immunodeficiency Virus (HIV), but also by their improved ability to inhibit the replication of mutant strains, in particular strains which have become resistant to one or more known NNRTI drugs (Non Nucleoside Reverse Transcriptase Inhibitor drugs), which strains are referred to as drug or multidrug resistant HIV strains.

Thus in one aspect, the present invention concerns a compound of formula

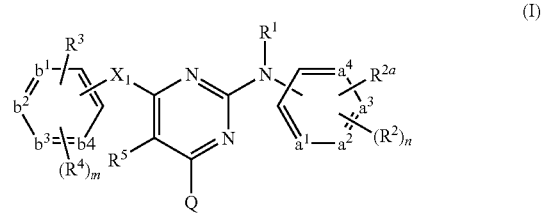

a N-oxide, a pharmaceutically acceptable addition salt, a quaternary amine or a stereochemically isomeric form thereof, wherein $-a^1=a^2-a^3=a^4-$ represents a bivalent radical of formula

| —CH=CH—CH=CH— | (a-1); |
|---|---|
| —N=CH—CH=CH— | (a-2); |
| —N=CH—N=CH— | (a-3); |
| —N=CH—CH=N— | (a-4); |
| —N=N—CH=CH— | (a-5); |

$-b^1=b^2-b^3=b^4-$ represents a bivalent radical of formula

| —CH=CH—CH=CH— | (b-1); |
|---|---|
| —N=CH—CH=CH— | (b-2); |
| —N=CH—N=CH— | (b-3); |
| —N=CH—CH=N— | (b-4); |
| —N=N—CH=CH— | (b-5); | n is 0, 1, 2, 3 and in case $-a^1=a^2-a^3=a^4-$ is (a-1), then n may also be 4;

m is 0, 1, 2, 3 and in case $-b^1=b^2-b^3=b^4-$ is (b-1), then m may also be 4;

each $R^1$ independently is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, or with $C_{1-6}$alkylcarbonyloxy;

each $R^2$ independently is hydroxy; halo; $C_{1-6}$alkyl optionally substituted with one, two or three substituents each independently selected from halo, cyano or —C(=O)$R^6$; $C_{3-7}$cycloalkyl; $C_{2-6}$alkenyl optionally substituted with one, two or three substituents each independently selected from halo, cyano or —C(=O)$R^6$; $C_{2-6}$alkynyl optionally substituted with one, two or three substituents each independently selected from halo, cyano or —C(=O)$R^6$; $C_{1-6}$alkyloxycarbonyl; carboxyl; cyano; nitro; amino; mono- or di($C_{1-6}$alkyl)amino; polyhalomethyl; polyhalomethylthio; —S(=O)r$R^6$; —NH—S(=O)r$R^6$; —C(=O)$R^6$; —NHC(=O)H; —C(=O)NHNH$_2$; NHC(=O)$R^6$; C(=NH)$R^6$;

$R^{2a}$ is cyano; aminocarbonyl; amino; $C_{1-6}$alkyl; halo; $C_{1-6}$alkyloxy wherein $C_{1-6}$alkyl may optionally be substituted with cyano; NHR$^{13}$; NR$^{13}$R$^{14}$; —C(=O)—NHR$^{13}$; —C(=O)—NR$^{13}$R$^{14}$; —C(=O)—R$^{15}$; —CH=N—NH—C(=O)—R$^{16}$; $C_{1-6}$alkyl substituted with one, two or three substituents each independently selected from halo, cyano, NR$^9$R$^{10}$, —C(=O)—NR$^9$R$^{10}$, —C(=O)—$C_{1-6}$alkyl or R$^7$; $C_{1-6}$alkyl substituted with hydroxy and a second substituent selected from halo, cyano, $NR^9R^{10}$, —C(=O)—$NR^9R^{10}$, —C(=O)—$C_{1-6}$alkyl or $R^7$; $C_{1-6}$alkyloxy$C_{1-6}$alkyl optionally substituted with one, two or three substituents each independently selected from halo, cyano, $NR^9R^{10}$, —C(=O)—$NR^9R^{10}$, —C(=O)—$C_{1-6}$alkyl or $R^7$; $C_{2-6}$alkenyl substituted with one, two or three substituents each independently selected from halo, cyano, $NR^9R^{10}$, —C(=O)—$NR^9R^{10}$, —C(=O)—$C_{1-6}$alkyl or $R^7$; $C_{2-6}$alkynyl substituted with one, two or three substituents each independently selected from halo, cyano, $NR^9R^{10}$, —C(=O)—$NR^9R^{10}$, —C(=O)—$C_{1-6}$alkyl or $R^7$; —C(=N—O—$R^8$)—$C_{1-4}$alkyl; $R^7$ or —$X_3$—$R^7$;

$X_1$ is —$NR^1$—, —O—, —C(=O)—, —$CH_2$—, —CHOH—, —S—, —S(=O)$_r$—,;

$R^3$ is cyano; aminocarbonyl; amino; $C_{1-6}$alkyl; halo; $C_{1-6}$alkyloxy wherein $C_{1-6}$alkyl may optionally be substituted with cyano; $NHR^{13}$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl substituted with one, two or three substituents each independently selected from halo, cyano, $NR^9R^{10}$, —C(=O)—$NR^9R^{10}$, —C(=O)—$C_{1-6}$alkyl or $R^7$; $C_{1-6}$alkyl substituted with hydroxy and a second substituent selected from halo, cyano, $NR^9R^{10}$, —C(=O)—$NR^9R^{10}$, —C(=O)—$C_{1-6}$alkyl or $R^7$; $C_{1-6}$alkyloxy$C_{1-6}$alkyl optionally substituted with one, two or three substituents each independently selected from halo, cyano, $NR^9R^{10}$, —C(=O)—$NR^9R^{10}$, —C(=O)—$C_{1-6}$alkyl or $R^7$; $C_{2-6}$alkenyl substituted with one, two or three substituents each independently selected from halo, cyano, $NR^9R^{10}$, —C(=O)—$NR^9R^{10}$, —C(=O)—$C_{1-6}$alkyl or $R^7$; $C_{2-6}$alkynyl substituted with one, two or three substituents each independently selected from halo, cyano, $NR^9R^{10}$, —C(=O)—$NR^9R^{10}$, —C(=O)—$C_{1-6}$alkyl or $R^7$; —C(=N—O—$R^8$)—$C_{1-4}$alkyl; $R^7$ or —$X_3$—$R^7$;

$X_3$ is —$NR^1$—, —O—, —C(=O)—, —S—, —S(=O)$_r$—;

$R^4$ is halo; hydroxy; $C_{1-6}$alkyl optionally substituted with one, two or three substituents each independently selected from halo, cyano or —C(=O)$R^6$; $C_{2-6}$alkenyl optionally substituted with one, two or three substituents each independently selected from halo, cyano or —C(=O)$R^6$; $C_{2-6}$alkynyl optionally substituted with one, two or three substituents each independently selected from halo, cyano or —C(=O)$R^6$; $C_{3-7}$cycloalkyl; $C_{1-6}$alkyloxy; cyano; nitro; polyhalo$C_{1-6}$alkyl; polyhalo$C_{1-6}$alkyloxy; aminocarbonyl; mono- or di($C_{1-4}$alkyl)aminocarbonyl; $C_{1-6}$alkyloxycarbonyl; $C_{1-6}$alkylcarbonyl; formyl; amino; mono- or di($C_{1-4}$alkyl)amino or $R^7$;

$R^5$ is a radical of formula —Y-Alk-L, -Alk'-Y-L or -Alk'-Y-Alk-L;

each Alk or Alk' independently is a bivalent $C_{1-6}$alkyl or $C_{2-6}$alkenyl group;

L is aryl or Het;

Y is O, S, —S(=O)$_r$—, $NR^1$; —CH=N—O—;

Het is a 5- or 6-membered completely unsaturated ring system wherein one, two, three or four ring members are hetero atoms each independently selected from the group consisting of nitrogen, oxygen and sulfur, and wherein the remaining ring members are carbon atoms; and, where possible, any nitrogen ring member may optionally be substituted with $C_{1-6}$alkyl; which ring system may optionally be annelated with a benzene ring; and wherein any ring carbon atom, including any carbon of an optionally annelated benzene ring, may, each independently, optionally be substituted with a substituent selected from halo, hydroxy, mercapto, cyano, $C_{1-6}$alkyl, hydroxy$C_{1-4}$alkyl, carboxy$C_{1-4}$alkyl, $C_{1-4}$alkyloxy$C_{1-4}$alkyl, $C_{1-4}$alkyloxycarbonyl$C_{1-4}$alkyl, cyano$C_{1-4}$alkyl, mono- and di($C_{1-4}$alkyl)amino$C_{1-4}$alkyl, $Het^1C_{1-4}$alkyl, aryl$C_{1-4}$alkyl, polyhalo$C_{1-4}$alkyl, $C_{3-7}$cycloalkyl, $C_{2-6}$alkenyl, aryl-$C_{2-4}$alkenyl, $C_{1-4}$alkyloxy, —$OCONH_2$, polyhalo-$C_{1-4}$alkyloxy, aryloxy, amino, mono- and di-$C_{1-4}$alkylamino, pyrrolidinyl, piperidinyl, morpholinyl, piperazinyl, 4-$C_{1-6}$alkylpiperazinyl, $C_{1-4}$alkylcarbonylamino, formyl, $C_{1-4}$alkylcarbonyl, $C_{1-4}$alkyloxy-carbonyl, aminocarbonyl, mono- and di$C_{1-4}$alkylaminocarbonyl, aryl, $Het^1$;

$Het^1$ is pyridyl, thienyl, furanyl, oxazolyl, isoxazolyl, imidazolyl, pyrazolyl, thiazolyl, thiadiazolyl, oxadiazolyl quinolinyl, benzothienyl, benzofuranyl; which each may optionally be substituted with one or two $C_{1-4}$alkyl radicals;

Q is hydrogen, $C_{1-6}$alkyl, halo, polyhalo$C_{1-6}$alkyl, or —$NR^9R^{10}$;

$R^6$ is $C_{1-4}$alkyl, amino, mono- or di($C_{1-4}$alkyl)amino or polyhalo$C_{1-4}$alkyl;

$R^7$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, —CH(=N—O—$R^8$), $R^{7a}$, —$X_3$—$R^{7a}$ or $R^{7a}$—$C_{1-4}$alkyl-;

$R^{7a}$ is a monocyclic, bicyclic or tricyclic saturated, partially saturated or aromatic carbocycle or a monocyclic, bicyclic or tricyclic saturated, partially saturated or aromatic heterocycle, wherein each of said carbocyclic or heterocyclic ring systems may optionally be substituted with one, two, three, four or five substituents each independently selected from halo, hydroxy, mercapto, $C_{1-6}$alkyl, hydroxy$C_{1-6}$alkyl, amino$C_{1-6}$alkyl, mono or di($C_{1-6}$alkyl)amino$C_{1-6}$alkyl, formyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, —CH(=N—O—$R^8$);

$R^8$ is hydrogen, $C_{1-4}$alkyl, aryl or aryl$C_{1-4}$alkyl;

$R^9$ and $R^{10}$ each independently are hydrogen; $C_{1-6}$alkyl; $C_{1-6}$alkylcarbonyl; $C_{1-6}$alkyloxycarbonyl; amino; mono- or di($C_{1-6}$alkyl)aminocarbonyl; —CH(=$NR^{11}$) or $R^7$, wherein each of the aforementioned $C_{1-6}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, mono- or di($C_{1-4}$alkyl)amino, polyhalomethyl, polyhalomethyloxy, polyhalomethylthio, —S(=O)$_r R^6$, —NH—S(=O)$_r R^6$, —C(=O)$R^6$, —NHC(=O)H, —C(=O)$NHNH_2$, —NHC(=O)$R^6$, —C(=NH)$R^6$, $R^7$; or $R^9$ and $R^{10}$ may be taken together to form a bivalent or trivalent radical of formula

| —$CH_2$—$CH_2$—$CH_2$—$CH_2$— | (d-1) |
| —$CH_2$—$CH_2$—$CH_2$—$CH_2$—$CH_2$— | (d-2) |
| —$CH_2$—$CH_2$—O—$CH_2$—$CH_2$— | (d-3) |
| —$CH_2$—$CH_2$—S—$CH_2$—$CH_2$— | (d-4) |
| —$CH_2$—$CH_2$—$NR^{12}$—$CH_2$—$CH_2$— | (d-5) |

—CH$_2$—CH═CH—CH$_2$— (d-6)

═CH—CH═CH—CH═CH— (d-7)

R$^{11}$ is cyano; C$_{1-4}$alkyl optionally substituted with C$_{1-4}$alkyloxy, cyano, amino, mono- or di(C$_{1-4}$alkyl)amino or aminocarbonyl; C$_{1-4}$alkylcarbonyl; C$_{1-4}$alkyloxycarbonyl; aminocarbonyl; mono- or di(C$_{1-4}$alkyl)aminocarbonyl;

R$^{12}$ is hydrogen or C$_{1-4}$alkyl;

R$^{13}$ and R$^{14}$ each independently are C$_{1-6}$alkyl optionally substituted with cyano or aminocarbonyl, C$_{2-6}$alkenyl optionally substituted with cyano or aminocarbonyl, C$_{2-6}$alkynyl optionally substituted with cyano or aminocarbonyl;

R$^{15}$ is C$_{1-6}$alkyl substituted with cyano or aminocarbonyl;

R$^{16}$ is C$_{1-6}$alkyl optionally substituted with cyano or aminocarbonyl, or R$^7$;

each r is 1 or 2;

each aryl is phenyl or phenyl substituted with one, two, three, four or five substituents each independently selected from halo, hydroxy, mercapto, C$_{1-6}$alkyl, C$_{2-6}$alkenyl, C$_{2-6}$alkynyl, hydroxyC$_{1-6}$alkyl, aminoC$_{1-6}$alkyl, mono or di(C$_{1-6}$alkyl)amino-C$_{1-6}$alkyl, C$_{1-6}$alkylcarbonyl, C$_{3-7}$cycloalkyl, C$_{1-6}$alkyloxy, phenylC$_{1-6}$alkyloxy, C$_{1-6}$alkyloxycarbonyl, aminosulfonyl, C$_{1-6}$alkylthio, cyano, nitro, polyhaloC$_{1-6}$alkyl, polyhaloC$_{1-6}$alkyloxy, aminocarbonyl, phenyl, Het$^1$ or —X$_3$-Het$^1$.

The present invention also relates to the use of a compound for the manufacture of a medicament for the treatment or prevention of HIV infection, wherein the compound has the formula (I) as specified herein.

As used hereinbefore or hereinafter C$_{1-4}$alkyl as a group or part of a group defines straight or branched chain saturated hydrocarbon radicals having from 1 to 4 carbon atoms such as methyl, ethyl, propyl, 1-methylethyl, butyl; C$_{1-6}$alkyl as a group or part of a group defines straight or branched chain saturated hydrocarbon radicals having from 1 to 6 carbon atoms such as the group defined for C$_{1-4}$alkyl and pentyl, hexyl, 2-methylbutyl and the like; C$_{2-6}$alkyl as a group or part of a group defines straight or branched chain saturated hydrocarbon radicals having from 2 to 6 carbon atoms such as ethyl, propyl, 1-methylethyl, butyl, pentyl, hexyl, 2-methylbutyl and the like; C$_{3-7}$cycloalkyl is generic to cyclopropyl, cyclobutyl, cyclopentyl, cyclohexyl and cycloheptyl; C$_{2-6}$alkenyl defines straight and branched chain hydrocarbon radicals having from 2 to 6 carbon atoms containing a double bond such as ethenyl, propenyl, butenyl, pentenyl, hexenyl and the like; C$_{2-6}$alkynyl defines straight and branched chain hydrocarbon radicals having from 2 to 6 carbon atoms containing a triple bond such as ethynyl, propynyl, butynyl, pentynyl, hexynyl and the like. Of interest amongst the C$_{2-6}$alkenyl and C$_{2-6}$alkynyl groups are the unsaturated analogs having from 2 to 4 carbon atoms, i.e. C$_{2-4}$alkenyl and C$_{2-4}$alkynyl respectively. C$_{2-6}$alkenyl and C$_{2-6}$alkynyl groups that are linked to a heteroatom are preferably linked to that atom via a saturated carbon atom and thereby are limited to C$_{3-6}$alkenyl and C$_{3-6}$alkynyl groups.

The term "bivalent C$_{1-6}$alkyl or C$_{2-6}$alkenyl" refers to bivalent radicals which otherwise can also be referred to as C$_{1-6}$alkanediyl or C$_{2-6}$alkenediyl. The term bivalent C$_{1-6}$alkyl or C$_{1-6}$alkanediyl defines straight or branched chain saturated bivalent hydrocarbon radicals having from 1 to 6 carbon atoms such as methylene, 1,2-ethanediyl or 1,2-ethylene, 1,3-propanediyl or 1,3-propylene, 1,2-propanediyl or 1,2-propylene, 1,4-butanediyl or 1,4-butylene, 1,3-butanediyl or 1,3-butylene, 1,2-butanediyl or 1,2-butylene, 1,5-pentanediyl or 1,5-pentylene, 1,6-hexanediyl or 1,6-hexylene, etc., also including the alkylidene radicals such as ethylidene, propylidene and the like. The term bivalent C$_{1-4}$alkyl or C$_{1-4}$alkanediyl defines the analogous straight or branched chain saturated bivalent hydrocarbon radicals having from 1 to 4 carbon atoms. The term bivalent C$_{2-6}$alkenyl or C$_{2-6}$alkenediyl defines straight or branched chain bivalent hydrocarbon radicals having from 1 to 6 carbon atoms and having one or more (e.g. one, two, three) and preferably one double bond such as ethene-1,2-diyl, propene-1,3-diyl, propene-1,2-diyl, butene-1,4-diyl, 2-butene-1,4-diyl, butene-1,3-diyl, butene-3,4-diyl, butene-4,4-diyl, pentene-1,5-diyl, 2-pentene-1,5-diyl, hexene-1,6-diyl, 2-hexene-1,6-diyl, 3-hexene-1,6-diyl, etc. The term bivalent C$_{3-6}$alkenyl or C$_{3-6}$alkenediyl defines the analogous straight or branched chain bivalent unsaturated hydrocarbon radicals having from 3 to 6 carbon atoms while the term bivalent C$_{3-4}$alkenyl or C$_{3-4}$alkenediyl defines the analogous straight or branched chain bivalent unsaturated hydrocarbon radicals having from 3 to 4 carbon atoms. Of particular interest are bivalent C$_{3-6}$alkenyl or bivalent C$_{3-4}$alkenyl radicals, in particular those wherein the carbon atom linked to a heteroatom is a saturated carbon atom.

In a number of instances the radicals C$_{1-6}$alkyl, C$_{2-6}$alkenyl, C$_{2-6}$alkynyl or C$_{1-6}$alkyloxyC$_{1-6}$alkyl may be substituted with one, two or three substituents. Preferably, said radicals are substituted with up to 2 substituents, more preferably with one substituent.

A monocyclic, bicyclic or tricyclic saturated carbocycle represents a ring system consisting of 1, 2 or 3 rings, said ring system being composed of only carbon atoms and said ring system containing only single bonds; a monocyclic, bicyclic or tricyclic partially saturated carbocycle represents a ring system consisting of 1, 2 or 3 rings, said ring system being composed of only carbon atoms and comprising at least one double bond provided that the ring system is not an aromatic ring system; a monocyclic, bicyclic or tricyclic aromatic carbocycle represents an aromatic ring system consisting of 1, 2 or 3 rings, said ring system being composed of only carbon atoms; the term aromatic is well known to a person skilled in the art and designates cyclically conjugated systems of 4n+2 electrons, that is with 6, 10, 14 etc. π-electrons (rule of Hückel); a monocyclic, bicyclic or tricyclic saturated heterocycle represents a ring system consisting of 1, 2 or 3 rings and comprising at least one heteroatom selected from O, N or S, said ring system containing only single bonds; a monocyclic, bicyclic or tricyclic partially saturated heterocycle represents a ring system consisting of 1, 2 or 3 rings and comprising at least one heteroatom selected from O, N or S, and at least one double bond provided that the ring system is not an aromatic ring system; a monocyclic, bicyclic or tricyclic aromatic heterocycle represents an aromatic ring system consisting of 1, 2 or 3 rings and comprising at least one heteroatom selected from O, N or S.

Particular examples of monocyclic, bicyclic or tricyclic saturated carbocycles are cyclopropyl, cyclobutyl, cyclopentyl, cyclohexyl, cycloheptyl, cyclooctyl, bicyclo[4,2,0]octanyl, cyclononanyl, cyclodecanyl, decahydronapthalenyl, tetradecahydroanthracenyl and the like. Preferred are cyclopropyl, cyclobutyl, cyclopentyl, cyclohexyl, cycloheptyl; more preferred are cyclopentyl, cyclohexyl, cycloheptyl.

Particular examples of monocyclic, bicyclic or tricyclic partially saturated carbocycles are cyclopropenyl, cyclobutenyl, cyclopentenyl, cyclohexenyl, cycloheptenyl, cyclooctenyl, bicyclo[4,2,0]octenyl, cyclononenyl, cyclodecenyl, octahydronaphthalenyl, 1,2,3,4-tetrahydronaphthalenyl, 1,2,3,4,4a,9,9a,10-octahydro-anthracenyl and the like.

Particular examples of monocyclic, bicyclic or tricyclic aromatic carbocycles are phenyl, naphthalenyl, anthracenyl. Preferred is phenyl.

Particular examples of monocyclic, bicyclic or tricyclic saturated heterocycles are tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyrazinyl, dioxanyl, morpholinyl, dithianyl, thiomorpholinyl, piperazinyl, trithianyl, decahydroquinolinyl, octahydroindolyl and the like. Preferred are tetrahydrofuranyl, pyrrolidinyl, dioxolanyl, imidazolidinyl, thiazolidinyl, dihydrooxazolyl, triazolidinyl, piperidinyl, dioxanyl, morpholinyl, thiomorpholinyl, piperazinyl. Particularly preferred are tetrahydrofuranyl, pyrrolidinyl, dioxolanyl, piperidinyl, dioxanyl, morpholinyl, thiomorpholinyl, piperazinyl.

Particular examples of monocyclic, bicyclic or tricyclic partially saturated heterocycles are pyrrolinyl, imidazolinyl, pyrazolinyl, 2,3-dihydrobenzofuranyl, 1,3-benzodioxolyl, 2,3-dihydro-1,4-benzodioxinyl, indolinyl and the like. Preferred are pyrrolinyl, imidazolinyl, 2,3-dihydrobenzofuranyl, 1,3-benzodioxolyl, indolinyl.

Particular examples of monocyclic, bicyclic or tricyclic aromatic heterocycles are azetyl, oxetylidenyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, phthalazinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, isoxazolotriazinyl, isothiazolotriazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, phenoxazinyl and the like.

Preferred aromatic heterocycles are monocyclic or bicyclic aromatic heterocycles. Interesting monocyclic, bicyclic or tricyclic aromatic heterocycles are pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, phthalazinyl, quinoxalinyl, quinazolinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, carbazolyl, acridinyl, phenothiazinyl, phenoxazinyl and the like.

Particularly interesting aromatic heterocycles are pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, phthalazinyl, quinoxalinyl, quinazolinyl, and the like.

As used herein before, the term (=O) forms a carbonyl moiety when attached to a carbon atom, a sulfoxide moiety when attached to a sulfur atom and a sulfonyl moiety when two of said terms are attached to a sulfur atom.

The terms carboxyl, carboxy or hydroxycarbonyl refer to a group —COOH.

The term halo is generic to fluoro, chloro, bromo and iodo. As used in the foregoing and hereinafter, polyhalomethyl as a group or part of a group is defined as mono- or polyhalosubstituted methyl, in particular methyl with one or more fluoro atoms, for example, difluoromethyl or trifluoromethyl; polyhalo$C_{1-4}$alkyl or polyhalo$C_{1-6}$alkyl as a group or part of a group is defined as mono- or polyhalosubstituted $C_{1-4}$alkyl or $C_{1-6}$alkyl, for example, the groups defined in halomethyl, 1,1-difluoro-ethyl and the like. In case more than one halogen atoms are attached to an alkyl group within the definition of polyhalomethyl, polyhalo$C_{1-4}$alkyl or polyhalo$C_{1-6}$alkyl, they may be the same or different.

The radical Het is a 5- or 6-membered completely unsaturated ring system which may be annelated with a benzene ring as specified herein. The term completely unsaturated as used in this definition means that the ring contains the maximum number of double bonds. In many instances the said 5- or 6-membered ring system will be aromatic. Particular subgroups of compounds in accordance with the present invention therefore are those groups or subgroups as defined herein wherein Het is a 5- or 6-membered aromatic ring system as specified herein. The radical Het in particular may be any of the heterocycles mentioned in the groups of monocyclic, bicyclic or tricycles specified above, that are covered by the general definition of Het, e.g. pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, quinolinyl, isoquinolinyl, cinnolinyl, phthalazinyl, quinoxalinyl, quinazolinyl, naphthiridinyl, benzopyranyl.

The radical Het can be substituted with pyrrolidinyl, piperidinyl, morpholinyl, piperazinyl, 4-$C_{1-6}$alkylpiperazinyl. Preferably, these radicals are linked to the Het moiety via their nitrogen atom.

Whenever it occurs in the definition of the compounds of formula (I) or in any of the subgroups specified herein, each aryl independently is as defined above in the definition of the compounds of formulas (I) or each aryl can have any of the meanings specified hereinafter, in particular under the limitations (22), (22a), etc.

The term heterocycle in the definition of $R^7$ or $R^{7a}$ is meant to include all the possible isomeric forms of the heterocycles, for instance, pyrrolyl comprises 1H-pyrrolyl and 2H-pyrrolyl.

The carbocycle or heterocycle in the definition of $R^7$ or $R^{7a}$ may be attached to the remainder of the molecule of formula (I) through any ring carbon or heteroatom as appropriate, if not otherwise specified. Thus, for example, when the heterocycle is imidazolyl, it may be 1-imidazolyl, 2-imidazolyl, 4-imidazolyl and the like, or when the carbocycle is naphthalenyl, it may be 1-naphthalenyl, 2-naphthalenyl and the like.

When any variable (e.g. $R^7$, $X_2$) occurs more than one time in any constituent, each definition of such variable is independent.

Any of the restrictions in the definitions of the radicals herein are meant to be applicable to the group of compounds of formula (I) as well as to any subgroup defined or mentioned herein.

Lines drawn from substituents into ring systems indicate that the bond may be attached to any of the suitable ring atoms.

For therapeutic use, salts of the compounds of formula (I) are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form. The term addition salt also comprises the hydrates and solvent addition forms which the compounds of formula (I) are able to form. Examples of such forms are e.g. hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several tertiary nitrogen atoms are oxidized to the so-called N-oxide.

It will be appreciated that some of the compounds of formula (I) and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) and their N-oxides, salts, solvates or quaternary amines substantially free, i.e. associated with less than 10%, preferably less than 5%, in particular less than 2% and most preferably less than 1% of the other isomers. Thus, when a compound of formula (I) is for instance specified as (E), this means that the compound is substantially free of the (Z) isomer. In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art. Stereochemically isomeric forms of the compounds of formula (I) are intended to be embraced within the scope of this invention.

Some of the compounds of formula (I) may also exist in their tautomeric form. Such forms although not explicitly indicated in the above formula are intended to be included within the scope of the present invention.

Whenever used hereinafter, the term "compounds of formula (I)" is meant to also include their N-oxide forms, their salts, their quaternary amines and their stereochemically isomeric forms. Of special interest are those compounds of formula (I), which are stereochemically pure.

Particular subgroups of compounds of formula (I) or any of the subgroups of compounds of formula (I) specified herein which are the non-salt-forms, the salts, the N-oxide forms and stereochemically isomeric forms. Of interest amongst these are the non-salt-forms, the salts and stereochemically isomeric forms. As used herein, the term 'non-salt-form' refers to the form of a compound which is not a salt, which in most cases will be the free base form.

Whenever mention is made hereinbefore or hereinafter that substituents can be selected each independently out of a list of numerous definitions, such as for example for $R^9$ and $R^{10}$, all possible combinations are intended which are chemically possible or which lead to chemically stable molecules.

It is to be understood that any of the subgroups of compounds of formulae (I) as defined herein, are meant to also comprise any prodrugs, N-oxides, addition salts, quaternary amines, metal complexes and stereochemically isomeric forms of such compounds. Any further subgroup comprising a permutation of any of the more specific definitions of subgroups of compounds of formula (I) as mentioned hereafter, is meant to also form part of the disclosure of this invention.

Particular subgroups of the compounds of formula (I) are those compounds of formula (I), or any subgroup of compounds of formula (I) specified herein, wherein -$a^1$=$a^2$-$a^3$=$a^4$- is —CH=CH—CH=CH— (a-1);

Further subgroups of the compounds of formula (I) are those compounds of formula (I), or any subgroup of compounds of formula (I) specified herein, wherein -$b^1$=$b^2$-$b^3$=$b^4$- is —CH=CH—CH=CH— (b-1).

Further subgroups of the compounds of formula (I) are those compounds of formula (I), or any subgroup of compounds of formula (I) specified herein, wherein (a) n is 0, 1, 2, 3; or wherein (b) n is 0, 1 or 2; or (c) n is 0.

Other subgroups of the compounds of formula (I) are those compounds of formula (I), or any subgroup of compounds of formula (I) specified herein, wherein (a) m is 0, 1, 2, 3; or wherein (b) m is 0, 1 or 2; or (c) m is 2.

Still further subgroups of the compounds of formula (I) are those compounds of formula (I), or any subgroup of compounds of formula (I) specified herein, wherein (a) $R^1$ is hydrogen; formyl; $C_{1-6}$alkylcarbonyl; $C_{1-6}$alkyl; $C_{1-6}$alkyloxycarbonyl; or (b) $R^1$ is hydrogen; $C_{1-6}$alkyl; or (c) $R^1$ is hydrogen.

Still further subgroups of the compounds of formula (I) are those compounds of formula (I), or any subgroup of compounds of formula (I) specified herein, wherein (a) $R^2$ is hydroxy; halo; $C_{1-6}$alkyl optionally substituted with one substituent selected from halo, cyano or —C(=O)$R^6$; $C_{3-7}$cycloalkyl; $C_{2-6}$alkenyl optionally substituted with one substituent selected from halo, cyano or —C(=O)$R^6$; $C_{2-6}$alkynyl optionally substituted with one substituent selected from halo, cyano or —C(=O)$R^6$; $C_{1-6}$alkyloxycarbonyl; carboxyl; cyano; nitro; amino; mono- or di($C_{1-6}$alkyl)amino; polyhalomethyl; polyhalomethylthio; —S(=O)$_p$$R^6$; —NH—S(=O)$_p$$R^6$; —C(=O)$R^6$; —NHC(=O)H; —C(=O)NHNH$_2$; NHC(=O)$R^6$; C(=NH)$R^6$;

(b) $R^2$ is hydroxy; halo; $C_{1-6}$alkyl optionally substituted with one substituent selected from halo, cyano or —C(=O)$R^6$; $C_{2-6}$alkenyl optionally substituted with one substituent selected from halo, cyano or —C(=O)$R^6$; $C_{2-6}$alkynyl optionally substituted with one substituent selected from halo, cyano or —C(=O)$R^6$; $C_{1-6}$alkyloxycarbonyl; carboxyl; cyano; nitro; amino; mono- or di($C_{1-6}$alkyl)-amino; trifluoromethyl;

(c) $R^1$ is halo, $C_{1-6}$alkyl optionally substituted with cyano, $C_{2-6}$alkenyl optionally substituted with cyano, $C_{2-6}$alkynyl optionally substituted with cyano, $C_{1-6}$alkyloxycarbonyl, carboxyl, cyano, amino, mono($C_{1-6}$alkyl)amino, di($C_{1-6}$alkyl)amino;

(d) $R^2$ is halo, cyano, aminocarbonyl, $C_{1-6}$alkyloxy, $C_{1-6}$alkyl, $C_{1-6}$alkyl substituted with cyano or $C_{2-6}$alkenyl substituted with cyano;

(e) $R^2$ is halo, cyano, aminocarbonyl, $C_{1-4}$alkyl substituted with cyano or $C_{2-4}$alkenyl substituted with cyano;

(f) $R^2$ is cyano, aminocarbonyl; or (g) $R^2$ is cyano.

Still further subgroups of the compounds of formula (I) are those compounds of formula (I), or any subgroup of compounds of formula (I) specified herein, wherein (a) $R^{2a}$ is cyano; aminocarbonyl; amino; $C_{1-6}$alkyl; halo; $C_{1-6}$alkyloxy wherein $C_{1-6}$alkyl may optionally be substituted with cyano; NHR$^{13}$; NR$^{13}$R$^{14}$; —C(=O)—NHR$^{13}$; —C(=O)—NR$^{13}$R$^{14}$; —C(=O)—$R^5$; —CH=N—NH—C(=O)—$R^{16}$; $C_{1-6}$alkyl substituted with one substituent selected from halo, cyano, NR$^9$R$^{10}$, —C(=O)—NR$^9$R$^{10}$, —C(=O)—$C_{1-6}$alkyl or $R^7$; $C_{1-6}$alkyl substituted with hydroxy and a second substituent selected from halo, cyano, NR$^9$R$^{10}$, —C(=O)—NR$^9$R$^{10}$, —C(=O)—$C_{1-6}$alkyl or $R^7$; $C_{1-6}$alkyloxy$C_{1-6}$alkyl optionally substituted with one substituent selected from halo, cyano, NR$^9$R$^{10}$, —C(=O)—NR$^9$R$^{10}$, —C(=O)—$C_{1-6}$alkyl or $R^7$; $C_{2-6}$alkenyl substituted with one substituent selected from halo, cyano, NR$^9$R$^{10}$, —C(=O)—NR$^9$R$^{10}$, —C(=O)—$C_{1-6}$alkyl or $R^7$; $C_{2-6}$alkynyl substituted with one substituent selected from halo, cyano, NR$^9$R$^{10}$, —C(=O)—NR$^9$R$^{10}$, —C(=O)—$C_{1-6}$alkyl or $R^7$; —C(=N—O—$R^8$)—$C_{1-4}$alkyl; $R^7$ or —$X_3$—$R^7$;

(b) $R^{2a}$ is cyano; aminocarbonyl; amino; $C_{1-6}$alkyl; halo; $C_{1-6}$alkyloxy wherein $C_{1-6}$alkyl may optionally be substituted with cyano; NHR$^{13}$; NR$^{13}$R$^{14}$; —C(=O)—NHR$^{13}$; —C(=O)—NR$^{13}$R$^{14}$; —C(=O)—$R^{15}$; —CH=N—NH—C(=O)—$R^{16}$; $C_{1-6}$alkyl substituted with one substituent selected from halo, cyano, —C(=O)—NR$^9$R$^{10}$; $C_{1-6}$alkyl substituted with hydroxy and a second substituent selected from halo, cyano, —C(=O)—NR$^9$R$^{10}$; $C_{1-6}$alkyloxy$C_{1-6}$alkyl optionally substituted with one substituent selected from halo, cyano, —C(=O)—NR$^9$R$^{10}$; $C_{2-6}$alkenyl substituted with one substituent selected from halo, cyano, —C(=O)—NR$^9$R$^{10}$; $C_{2-6}$alkynyl substituted with one substituent selected from halo, cyano, —C(=O)—NR$^9$R$^{10}$;

(c) $R^{2a}$ is halo, cyano, aminocarbonyl, $C_{1-6}$alkyl optionally substituted with cyano or aminocarbonyl, $C_{2-6}$alkenyl optionally substituted with cyano or aminocarbonyl;

(d) $R^{2a}$ is halo, cyano, aminocarbonyl, $C_{1-6}$alkyl substituted with cyano or aminocarbonyl, or $C_{2-6}$alkenyl substituted with cyano or aminocarbonyl;

(e) $R^{2a}$ is cyano, aminocarbonyl, $C_{1-6}$alkyl substituted with cyano or $C_{2-6}$alkenyl substituted with cyano;

(f) $R^{2a}$ is cyano, aminocarbonyl, $C_{1-4}$alkyl substituted with cyano or $C_{2-4}$alkenyl substituted with cyano;

(g) $R^{2a}$ is cyano, $C_{1-4}$alkyl substituted with cyano or $C_{2-4}$alkenyl substituted with cyano; or (h) $R^{2a}$ is cyano.

Still further subgroups of the compounds of formula (I) are those compounds of formula (I), or any subgroup of compounds of formula (I) specified herein, wherein (a) $X_1$ is —NR$^1$—, —O—, —S—, —S(=O)$_p$—;

(b) $X_1$ is —NH—, —N($C_{1-4}$alkyl)-, —O—, —S—, —S(=O)$_p$—;

(c) $X_1$ is —NH—, —N(CH$_3$)—, —O—, —S—; (d) $X_1$ is —NH—, —O—, —S—;

(e) $X_1$ is —NH—, —O—; or (f) $X_1$ is —NH—.

Still other subgroups of the compounds of formula (I) are those compounds of formula (I), or any subgroup of compounds of formula (I) specified herein, wherein (a) $R^3$ is cyano; aminocarbonyl; amino; $C_{1-6}$alkyl; halo; $C_{1-6}$alkyloxy wherein $C_{1-6}$alkyl may optionally be substituted with cyano; NHR$^{13}$; NR$^{13}$R$^{14}$; —C(=O)—NHR$^{13}$; —C(=O)—NR$^{13}$R$^{14}$; —C(=O)—$R^{15}$; —CH=N—NH—C(=O)—$R^1$ 6; $C_{1-6}$alkyl substituted with one substituent selected from halo, cyano, $NR^9R^{10}$, —C(=O)—$NR^9R^{10}$, —C(=O)—$C_{1-6}$alkyl or $R^7$; $C_{1-6}$alkyl substituted with hydroxy and a second substituent selected from halo, cyano, $NR^9R^{10}$, —C(=O)—$NR^9R^{10}$, —C(=O)—$C_{1-6}$alkyl or $R^7$; $C_{1-6}$alkyloxy$C_{1-6}$alkyl optionally substituted with one substituent selected from halo, cyano, $NR^9R^{10}$, —C(=O)—$NR^9R^{10}$, —C(=O)—$C_{1-6}$alkyl or $R^7$; $C_{2-6}$alkenyl substituted with one substituent selected from halo, cyano, $NR^9R^{10}$, —C(=O)—$NR^9R^{10}$, —C(=O)—$C_{1-6}$alkyl or $R^7$; $C_{2-6}$alkynyl substituted with one substituent selected from halo, cyano, $NR^9R^{10}$, —C(=O)—$NR^9R^{10}$, —C(=O)—$C_{1-6}$alkyl or $R^7$; —C(=N—O—$R^8$)—$C_{1-4}$alkyl; $R^7$ or —$X_3$—$R^7$; in particular (b) $R^3$ is cyano; aminocarbonyl; amino; $C_{1-6}$alkyl; halo; $C_{1-6}$alkyloxy wherein $C_{1-6}$alkyl may optionally be substituted with cyano; $NHR^3$; $NR^{13}R^{14}$; —C(=O)—$NHR^{13}$; —C(=O)—$NR^{13}R^{14}$; —C(=O)—$R^{15}$; —CH=N—NH—C(=O)—$R^{16}$; $C_{1-6}$alkyl substituted with one substituent selected from halo, cyano, —C(=O)—$NR^9R^{10}$; $C_{1-6}$alkyl substituted with hydroxy and a second substituent selected from halo, cyano, —C(=O)—$NR^9R^{10}$; $C_{1-6}$alkyloxy$C_{1-6}$alkyl optionally substituted with one substituent selected from halo, cyano, —C(=O)—$NR^9R^{10}$; $C_{2-6}$alkenyl substituted with one substituent selected from halo, cyano, —C(=O)—$NR^9R^{10}$; $C_{2-6}$alkynyl substituted with one substituent selected from halo, cyano, —C(=O)—$NR^9R^{10}$;

(c) $R^3$ is halo, cyano, aminocarbonyl, $C_{1-6}$alkyl optionally substituted with cyano or aminocarbonyl, $C_{2-6}$alkenyl optionally substituted with cyano or aminocarbonyl;

(d) $R^3$ is halo, cyano, aminocarbonyl, $C_{1-6}$alkyl substituted with cyano or aminocarbonyl, or $C_{2-6}$alkenyl substituted with cyano or aminocarbonyl;

(e) $R^3$ is cyano, $C_{1-4}$alkyl substituted with cyano or $C_{2-4}$alkenyl substituted with cyano;

(f) $R^3$ is $C_{1-4}$alkyl substituted with cyano or $C_{2-4}$alkenyl substituted with cyano;

(g) $R^3$ is $C_{2-4}$alkyl substituted with cyano or $C_{2-4}$alkenyl substituted with cyano;

(h) $R^3$ is $C_{2-4}$alkenyl substituted with cyano;

(i) $R^3$ is ethenyl substituted with cyano;

(j) $R^3$ is (E)-2-cyanoethenyl.

Still further subgroups of the compounds of formula (I) are those compounds of formula (I), or any subgroup of compounds of formula (I) specified herein, wherein (a) $R^4$ is halo; hydroxy; $C_{1-6}$alkyl optionally substituted with one substituent selected from halo, cyano or —C(=O)$R^6$; $C_{2-6}$alkenyl optionally substituted with one substituent selected from halo, cyano or —C(=O)$R^6$; $C_{2-6}$alkynyl optionally substituted with one substituent selected from halo, cyano or —C(=O)$R^6$; $C_{3-7}$cycloalkyl; $C_{1-6}$alkyloxy; cyano; nitro; polyhalo$C_{1-6}$alkyl; polyhalo$C_{1-6}$alkyloxy; aminocarbonyl; mono- or di($C_{1-4}$alkyl)aminocarbonyl; $C_{1-6}$alkyloxycarbonyl; $C_{1-6}$alkylcarbonyl; formyl; amino; mono- or di($C_{1-4}$alkyl)amino or $R^7$;

(b) $R^4$ is halo; hydroxy; $C_{1-6}$alkyl optionally substituted with one substituent selected from cyano; $C_{2-6}$alkenyl optionally substituted with cyano; $C_{2-6}$alkynyl optionally substituted with cyano; $C_{3-7}$cycloalkyl; $C_{1-6}$alkyloxy; cyano; nitro; trifluoromethyl; aminocarbonyl; mono- or di($C_{1-4}$alkyl)aminocarbonyl; $C_{1-6}$alkyloxycarbonyl; $C_{1-6}$alkylcarbonyl; formyl; amino; mono- or di($C_{1-4}$alkyl)amino or $R^7$;

(c) $R^4$ is halo; hydroxy; $C_{1-6}$alkyl optionally substituted with cyano; $C_{2-6}$alkenyl optionally substituted with cyano; $C_{2-6}$alkynyl optionally substituted with cyano; $C_{1-6}$alkyloxy; cyano; nitro; trifluoromethyl; aminocarbonyl; mono- or di($C_{1-4}$alkyl)aminocarbonyl; $C_{1-6}$-alkyloxycarbonyl; $C_{1-6}$alkylcarbonyl; formyl; amino; mono- or di($C_{1-4}$alkyl) amino;

(d) $R^4$ is halo, hydroxy, $C_{1-6}$alkyl, $C_{2-6}$alkenyl, $C_{2-6}$alkynyl, $C_{1-6}$alkyloxy, cyano, nitro, amino;

(e) $R^4$ is halo, hydroxy, $C_{1-4}$alkyl, $C_{1-4}$alkyloxy, cyano; or (f) $R^4$ is halo, $C_{1-4}$alkyl, $C_{1-4}$alkyloxy.

Further subgroups of the compounds of formula (I) are those compounds of formula (I), or any subgroup of compounds of formula (I) specified herein, wherein (a) $R^5$ is a radical of formula —Y-Alk-L, or -Alk'-Y-Alk-L;

(b) $R^5$ is a radical of formula —Y-Alk-L, or -Alk'-Y-Alk-L; wherein L is Het;

(c) $R^5$ is a radical of formula -Alk'-Y-L;

(d) $R^5$ is a radical of formula -Alk'-Y-L; wherein L is aryl.

Still further subgroups of the compounds of formula (I) are those compounds of formula (I), or any subgroup of compounds of formula (I) specified herein, wherein $R^5$ is a radical of formula —Y—$C_pH_{2p}$-L or —$C_qH_{2q}$—Y—$C_pH_{2p}$-L; wherein L is aryl or Het; wherein aryl, Het and Y are as specified above or hereinafter; and wherein p is 1-6;
q is 1-6;

and wherein in particular:

(a) Y is O, S, $NR^1$; —CH=N—O—; (b) Y is O, $NR^1$; —CH=N—O—; (c) Y is $NR^1$ or —CH=N—O—;

(b) p is 1-4; or in particular p is 1-2;

(c) q is 1-4; or in particular q is 1-2;

Still further subgroups of the compounds of formula (I) are those compounds of formula (I), or any subgroup of compounds of formula (I) specified herein, wherein (a) Het is a 5- or 6-membered completely unsaturated ring system wherein one, two, three or four ring members are hetero atoms each independently selected from the group consisting of nitrogen, oxygen and sulfur, and wherein the remaining ring members are carbon atoms; and, where possible, any nitrogen ring member may optionally be substituted with $C_{1-6}$alkyl; which ring system may optionally be annelated with a benzene ring; and wherein any ring carbon atom, including any carbon of an optionally annelated benzene ring, may, each independently, optionally be substituted with a substituent selected from halo, hydroxy, mercapto, cyano, $C_{1-6}$alkyl, hydroxy$C_{1-4}$alkyl, carboxy$C_{1-4}$alkyl, $C_{1-4}$alkyloxy-$C_{1-4}$alkyl, cyano$C_{1-4}$alkyl, di($C_{1-4}$alkyl)amino$C_{1-4}$alkyl, $Het^1C_{1-4}$alkyl, aryl-$C_{1-4}$alkyl, polyhalo$C_{1-4}$alkyl, $C_{3-7}$cycloalkyl, aryl-$C_{2-4}$alkenyl, $C_{1-4}$alkyloxy, —OCONH$_2$, polyhalo$C_{1-4}$alkyloxy, aryloxy, amino, mono- and di-$C_{1-4}$alkylamino, $C_{1-4}$alkylcarbonylamino, formyl, $C_{1-4}$alkylcarbonyl, aryl, $Het^1$;

(b) Het is a heterocycle selected from pyrrolyl, furanyl, thienyl, pyrazolyl, imidazolyl, oxazolyl, isoxazolyl, thiazolyl, isothiazolyl, triazolyl, tetrazolyl, thiatriazolyl, thiadiazolyl, oxadiazolyl, pyridyl, pyrimidinyl, pyrazinyl, pyridazinyl, benzofuranyl, benzothienyl, benzimidazolyl, benzoxazolyl, benzothiazolyl, benzotriazolyl, indolyl, benzothiadiazolyl, benzofurazanyl, benzoxadiazolyl, indazolyl, quinolinyl, said heterocycle optionally being substituted on its carbon atoms with one, two or three substituents each independently selected from halo, hydroxy, mercapto, cyano, $C_{1-6}$alkyl, hydroxy$C_{1-4}$alkyl, carboxy$C_{1-4}$alkyl, $C_{1-4}$alkyloxy$C_{1-4}$alkyl, $C_{1-4}$alkyloxycarbonyl-$C_{1-4}$alkyl, cyano$C_{1-4}$alkyl, mono- and di($C_{1-4}$alkyl)amino$C_{1-4}$alkyl, $Het^1C_{1-4}$alkyl, aryl$C_{1-4}$alkyl, polyhalo$C_{1-4}$alkyl, $C_{3-7}$cycloalkyl, aryl$C_{2-4}$alkenyl, $C_{1-4}$alkyloxy, —OCONH$_2$, polyhalo$C_{1-4}$alkyloxy, aryloxy, amino, mono- and di-$C_{1-4}$alkylamino, pyrrolidinyl, piperidinyl, morpholinyl, piperazinyl, 4-$C_{1-6}$alkylpiperazinyl, $C_{1-4}$alkylcarbonylamino, formyl, $C_{1-4}$alkylcarbonyl, aryl, $C_{1-4}$alkyloxycarbonyl, aminocarbonyl, mono- and di$C_{1-4}$alkylaminocarbonyl, Het$^1$;

(c) Het is a heterocycle selected from pyrrolyl, furanyl, thienyl, pyrazolyl, imidazolyl, oxazolyl, isoxazolyl, thiazolyl, isothiazolyl, triazolyl, tetrazolyl, thiatriazolyl, thiadiazolyl, oxadiazolyl, pyridyl, pyrimidinyl, pyrazinyl, pyridazinyl, benzofuranyl, indolyl, benzothiadiazolyl, quinolinyl, said heterocycle optionally being substituted on its carbon atoms with one, two or three substituents each independently selected from halo, hydroxy, cyano, $C_{1-6}$alkyl, $C_{1-4}$alkyloxycarbonyl-$C_{1-4}$alkyl, amino, mono- and di-$C_{1-4}$alkylamino, morpholinyl, $C_{1-4}$alkylcarbonylamino, aminocarbonyl, mono- and di$C_{1-4}$alkylaminocarbonyl, aryl, Het$^1$;

(d) Het is a heterocycle selected from pyrrolyl, furanyl, thienyl, isothiazolyl, thiatriazolyl, thiadiazolyl, oxadiazolyl, pyridyl, pyrimidinyl, benzofuranyl, quinolinyl, said heterocycle optionally being substituted on its carbon atoms with one, two or three substituents each independently selected from halo, hydroxy, cyano, $C_{1-6}$alkyl, $C_{1-4}$alkyloxycarbonyl-$C_{1-4}$alkyl, amino, mono- and di-$C_{1-4}$alkylamino, morpholinyl, $C_{1-4}$alkylcarbonylamino, aminocarbonyl, aryl phenyl, Het$^1$ (the latter in particular being pyridyl);

(e) Het is a heterocycle selected from pyrrolyl, furanyl, thienyl, oxadiazolyl, pyridyl, said heterocycle optionally being substituted on its carbon atoms with one, two or three substituents each independently selected from halo, hydroxy, $C_{1-6}$alkyl, phenyl, Het$^1$ (the latter in particular being pyridyl).

Still further subgroups of the compounds of formula (I) are those compounds of formula (I), or any subgroup of compounds of formula (I) specified herein, wherein (a) Het$^1$ is pyridyl, thienyl, furanyl, oxazolyl, isoxazolyl, imidazolyl, pyrazolyl, thiazolyl, thiadiazolyl, oxadiazolyl; which each may optionally be substituted with one or two $C_{1-4}$alkyl radicals;

(b) Het$^1$ is pyridyl, thienyl, furanyl; which each may optionally be substituted with one or two $C_{1-4}$alkyl radicals; or (c) Het$^1$ is pyridyl, thienyl, furanyl;

(d) Het$^1$ is pyridyl.

Still further subgroups of the compounds of formula (I) are those compounds of formula (I), or any subgroup of compounds of formula (I) specified herein, wherein (a) Q is hydrogen, $C_{1-6}$alkyl or —NR$^9$R$^{10}$; (b) Q is hydrogen or —NR$^9$R$^{10}$;

(c) Q is hydrogen, amino, mono- or di-$C_{1-4}$alkylamino; or (d) Q is hydrogen.

Other subgroups of the compounds of formula (I) are those compounds of formula (I), or any subgroup of compounds of formula (I) specified herein, wherein (a) R$^6$ is $C_{1-4}$alkyl, amino, mono- or di($C_{1-4}$alkyl)amino; in particular (b) R$^6$ is $C_{1-4}$alkyl or amino; or (c) R$^6$ is $C_{1-4}$alkyl.

Still further subgroups of the compounds of formula (I) are those compounds of formula (I), or any subgroup of compounds of formula (I) specified herein, wherein (a) R$^7$ is a monocyclic or bicyclic, partially saturated or aromatic carbocycle or a monocyclic or bicyclic, partially saturated or aromatic heterocycle, wherein each of said carbocyclic or heterocyclic ring systems may optionally be substituted with one, two or three substituents each independently selected from halo, hydroxy, mercapto, $C_{1-6}$alkyl, hydroxy$C_{1-6}$alkyl, amino$C_{1-6}$alkyl, $C_{1-6}$alkylcarbonyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy or aminocarbonyl; in particular (b) R$^7$ is any of the specific monocyclic or bicyclic, partially saturated or aromatic carbocycles or monocyclic or bicyclic, partially saturated or aromatic heterocycles specifically mentioned in this specification, wherein each of said carbocyclic or heterocyclic ring systems may optionally be substituted with one, two or three substituents each independently selected from halo, hydroxy, mercapto, $C_{1-6}$alkyl, hydroxy$C_{1-6}$alkyl, amino$C_{1-6}$alkyl, $C_{1-6}$alkylcarbonyl, $C_{1-6}$alkyloxy, $C_{1-6}$alkyloxycarbonyl, $C_{1-6}$alkylthio, cyano, nitro, polyhalo-$C_{1-6}$alkyl, polyhalo$C_{1-6}$alkyloxy or aminocarbonyl;

(c) R$^{7a}$ is a monocyclic or bicyclic, partially saturated or aromatic carbocycle or a monocyclic or bicyclic, partially saturated or aromatic heterocycle, wherein each of said carbocyclic or heterocyclic ring systems may optionally be substituted with one, two or three substituents each independently selected from halo, hydroxy, mercapto, $C_{1-6}$alkyl, hydroxy$C_{1-6}$alkyl, amino$C_{1-6}$alkyl, $C_{1-6}$alkylcarbonyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy or aminocarbonyl; in particular (d) R$^{7a}$ is any of the specific monocyclic or bicyclic, partially saturated or aromatic carbocycles or monocyclic or bicyclic, partially saturated or aromatic heterocycles specifically mentioned in this specification, wherein each of said carbocyclic or heterocyclic ring systems may optionally be substituted with one, two or three substituents each independently selected from halo, hydroxy, mercapto, $C_{1-6}$alkyl, hydroxy$C_{1-6}$alkyl, amino$C_{1-6}$alkyl, $C_{1-6}$alkylcarbonyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy or aminocarbonyl.

Further subgroups of the compounds of formula (I) are those compounds of formula (I), or any subgroup of compounds of formula (I) specified herein, wherein (a) $X_3$ is —NR$^1$—, —O— or —S—; (b) $X_3$ is —NR$^1$— or —O—; (c) $X_3$ is —NH—, —N($C_{1-4}$alkyl)-, —O—;

(d) $X_3$ is —NH—, —N(CH$_3$)—, —O—; or (e) $X_3$ is —NH—, —O—.

Other subgroups of the compounds of formula (I) are those compounds of formula (I), or any subgroup of compounds of formula (I) specified herein, wherein (a) R$^8$ is hydrogen, $C_{1-4}$alkyl or aryl$C_{1-4}$alkyl; or (b) R$^8$ is hydrogen or $C_{1-4}$alkyl.

Other subgroups of the compounds of formula (I) are those compounds of formula (I), or any subgroup of compounds of formula (I) specified herein, wherein (a) R$^9$ and R$^{10}$ each independently are hydrogen; $C_{1-6}$alkyl; $C_{1-6}$alkylcarbonyl; $C_{1-6}$alkyloxycarbonyl; mono- or di($C_{1-6}$alkyl)aminocarbonyl; —CH(=NR$^{11}$), wherein each of the aforementioned $C_{1-6}$alkyl groups may optionally be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, mono- or di($C_{1-14}$alkyl)amino, polyhalomethyl, polyhalomethyloxy;

(b) R$^9$ and R$^{10}$ each independently are hydrogen; $C_{1-6}$alkyl; $C_{1-6}$alkylcarbonyl or $C_{1-6}$alkyloxycarbonyl;

(c) $R^9$ and $R^{10}$ each independently are hydrogen or $C_{1-6}$alkyl;
(d) $R^9$ and $R^{10}$ are hydrogen.

Still other subgroups of the compounds of formula (I) are those compounds of formula (I), or any subgroup of compounds of formula (I) specified herein, wherein
(a) $R^{13}$ and $R^{14}$ each independently are $C_{1-6}$alkyl optionally substituted with cyano, $C_{2-6}$alkenyl optionally substituted with cyano, $C_{2-6}$alkynyl optionally substituted with cyano;
(b) $R^{13}$ and $R^{14}$ each independently are hydrogen or $C_{1-6}$alkyl;
(c) $R^{13}$ and $R^{14}$ are hydrogen.

Still other subgroups of the compounds of formula (I) are those compounds of formula (I), or any subgroup of compounds of formula (I) specified herein, wherein $R^{15}$ is $C_{1-6}$alkyl optionally substituted with cyano.

Still other subgroups of the compounds of formula (I) are those compounds of formula (I), or any subgroup of compounds of formula (I) specified herein, wherein (a) $R^{16}$ is $C_{1-6}$alkyl optionally substituted with cyano or aminocarbonyl; or wherein (b) $R^{16}$ is $C_{1-6}$alkyl optionally substituted with cyano.

Still other subgroups of the compounds of formula (I) are those compounds of formula (I), or any subgroup of compounds of formula (I) specified herein, wherein
(a) aryl is phenyl or phenyl substituted with one, two, three, four or five substituents each independently selected from halo, hydroxy, mercapto, $C_{1-6}$alkyl, hydroxy-$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, Het$^1$ or —$X_3$-Het$^1$.
(b) aryl is phenyl or phenyl substituted with one, two or three substituents each independently selected from halo, hydroxy, mercapto, $C_{1-6}$alkyl, hydroxy-$C_{1-6}$alkyl, amino$C_{1-6}$alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, $C_{1-6}$alkyloxycarbonyl, $C_{1-6}$alkylthio, cyano, nitro, polyhalo$C_{1-6}$alkyl, polyhalo$C_{1-6}$alkyloxy, aminocarbonyl, phenyl, thienyl or pyridyl;
(c) aryl is phenyl or phenyl substituted with one, two or three substituents each independently selected from halo, hydroxy, mercapto, $C_{1-6}$alkyl, hydroxy-$C_{1-6}$alkyl, amino$C_{1-6}$alkyl, mono or di($C_{1-6}$alkyl)amino $C_{1-6}$alkyl, $C_{1-6}$alkylcarbonyl, $C_{1-6}$alkyloxy, $C_{1-6}$alkyloxycarbonyl, $C_{1-6}$alylthio, cyano, nitro, trifluoromethyl, trifluoromethoxy, aminocarbonyl, phenyl;
(d) aryl is phenyl or phenyl substituted with one, two or three substituents each independently selected from halo, hydroxy, $C_{1-6}$alkyl, hydroxy$C_{1-6}$alkyl, amino $C_{1-6}$alkyl, mono or di($C_{1-6}$alkyl)amino $C_{1-6}$alkyl, $C_{1-6}$alkylcarbonyl, $C_{1-6}$alkyloxy, $C_{1-6}$alkyloxycarbonyl, cyano, nitro, trifluoromethyl;
(e) aryl is phenyl or phenyl substituted with one, two or three substituents each independently selected from halo, hydroxy, $C_{1-6}$alkyl, $C_{1-6}$alkyloxy, cyano, nitro, trifluoromethyl.

Whenever a radical or group occurs more than once in the definitions of the compounds of formula (I) each occurrence of said radical or group independently can have any of the definitions specified herein.

One embodiment concerns a subgroup of compounds of formula (I) having the formula

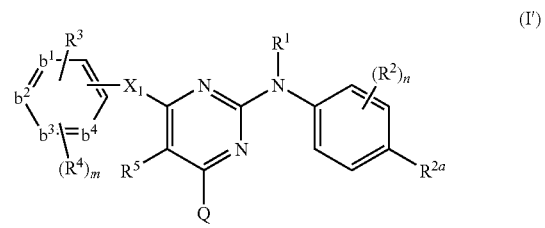

(I')

the N-oxides, the pharmaceutically acceptable addition salts, the quaternary amines or the stereochemically isomeric forms thereof, wherein -$b^1$=$b^2$-$b^3$=$b^4$-, $R^1$, $R^2$, $R^{2a}$, $R^3$, $R^4$, $R^5$, m, n and $X_1$ are as defined hereinabove in the general definition of the compounds of formula (I) or in the various subgroups thereof.

Yet another embodiment concerns a subgroup of compounds of formula (I) having the formula

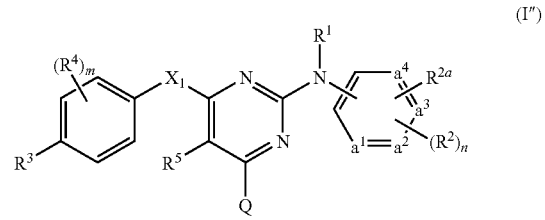

(I'')

the N-oxides, the pharmaceutically acceptable addition salts, the quaternary amines or the stereochemically isomeric forms thereof, wherein -$a^1$=$a^2$-$a^3$=$a^4$-, $R^1$, $R^2$, $R^{2a}$, $R^3$, $R^4$, $R^5$, m, n and $X_1$ are as defined hereinabove in the general definition of the compounds of formula (I) or in the various subgroups thereof.

Another embodiment concerns a subgroup of compounds of formula (I) having the formula

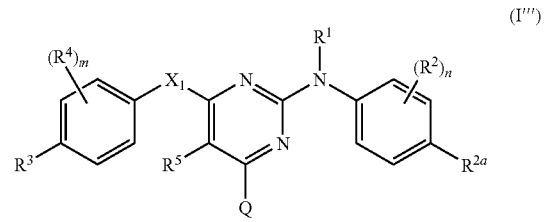

(I''')

the N-oxides, the pharmaceutically acceptable addition salts, the quaternary amines or the stereochemically isomeric forms thereof, wherein $R^1$, $R^2$, $R^{2a}$, $R^3$, $R^4$, $R^5$, m, n and $X_1$ are as defined hereinabove in the general definition of the compounds of formula (I) or in the various subgroups thereof.

A further embodiment encompasses a subgroup of compounds of formula (I) having the formula

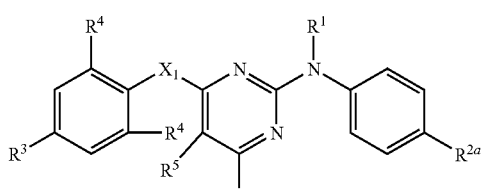

(I'''')

the N-oxides, the pharmaceutically acceptable addition salts, the quaternary amines or the stereochemically isomeric forms thereof, wherein $R^1$, $R^{2a}$, $R^3$, $R^4$, $R^5$ and $X_1$ are as defined hereinabove in the general definition of the compounds of formula (I) or in the various subgroups thereof.

Also an interesting embodiment encompasses a subgroup of compounds of formula (I) having the formula

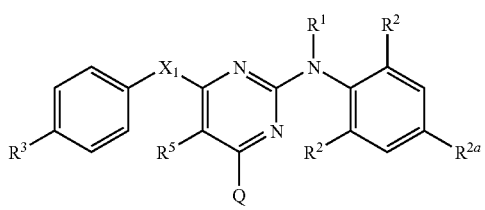

(I''''')

the N-oxides, the pharmaceutically acceptable addition salts, the quaternary amines or the stereochemically isomeric forms thereof, wherein $R^1$, $R^2$, $R^{2a}$, $R^3$, $R^5$ and $X_1$ are as defined hereinabove in the general definition of the compounds of formula (I) or in the various subgroups thereof.

The compounds of formula (I) can be prepared by reacting an intermediate of formula (II) wherein $W_1$ represents a suitable leaving group, such as for example halogen, e.g. chloro and the like, with an intermediate of formula (III).

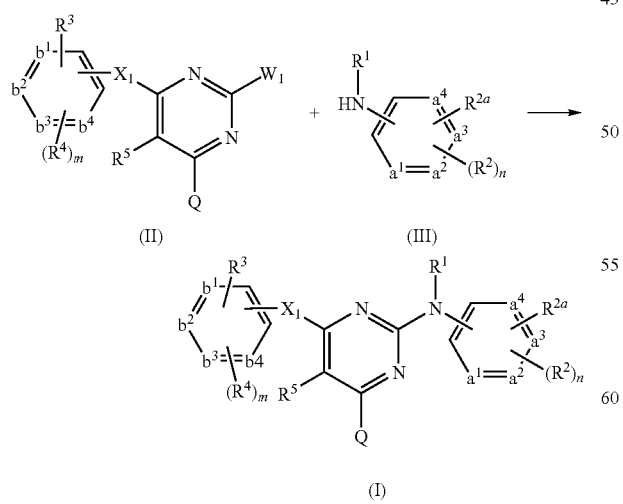

The reaction of the pyrimidine derivative (II) with the amine (III) is typically conducted in the presence of a suitable solvent. Suitable solvents are for example an alcohol, such as for example ethanol, 2-propanol; a dipolar aprotic solvent such as acetonitrile, N,N-dimethylformamide; N,N-dimethylacetamide, 1-methyl-2-pyrrolidinone; an ether such as tetrahydrofuran, 1,4-dioxane, propylene glycol monomethylether. The reaction may be done under acid conditions which may be obtained by adding amounts of a suitable acid, e.g. camphor sulfonic acid, and a suitable solvent, such as for example tetrahydrofuran or an alcohol, e.g. 2-propanol, or by using acidified solvents, e.g. hydrochloric acid dissolved in an alkanol such as 1- or 2-propanol.

The compounds of formula (I) can also be prepared by forming the $X_1$ linkage by either reacting (IV-a) with (V-a) or (IV-b) with (V-b) as outlined in the following scheme.

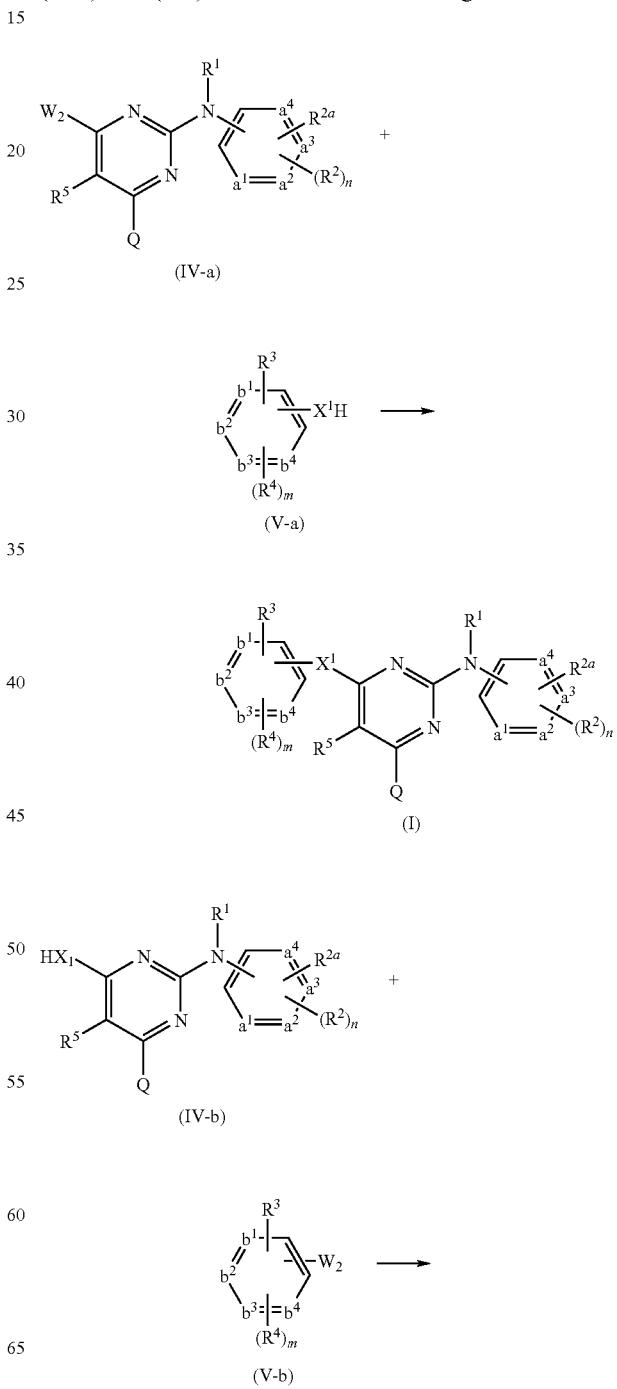

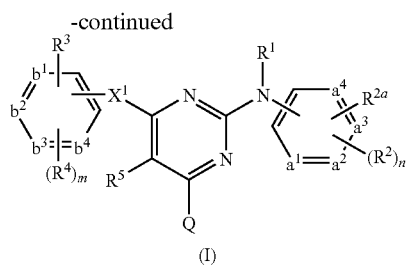

(I)

In this reaction scheme $W_2$ represents an appropriate functional group, which combined with the —$X_1H$ group can be transformed into an $X_1$ link. This procedure is most convenient for the preparation of compounds of formula (I) wherein $X_1$ is a heteroatom such as —$NR^1$—, —O—, —S—.

In particular, compounds of formula (I) wherein $X_1$ represents $NR^1$, said compounds being represented by formula (I-a), can be prepared by reacting an intermediate of formula (IV-c), wherein $W_1$ is an appropriate leaving group, e.g. chloro or bromo, with an intermediate of formula (V-c). The leaving group $W_1$ may also be introduced in situ, e.g. by converting the corresponding hydroxy function into a leaving group for example by $POCl_3$. The reaction of (IV-c) with (V-c) preferably is conducted in a suitable solvent in the presence of a base, e.g. triethylamine. Suitable solvents are for example acetonitrile, alcohols, such as for example ethanol, 2-propanol, ethylene glycol, propylene glycol, polar aprotic solvents such as N,N-dimethyl-formamide; N,N-dimethylacetamide, dimethylsufoxide, 1-methyl-2-pyrrolidinone, [bmim]$PF_5$; ethers such as 1,4-dioxane, propylene glycol monomethylether.

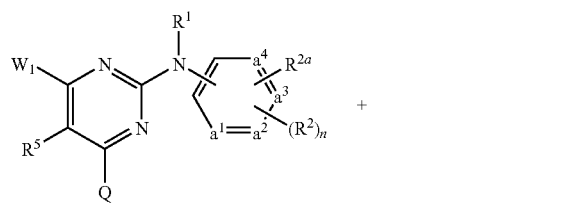

(IV-c)

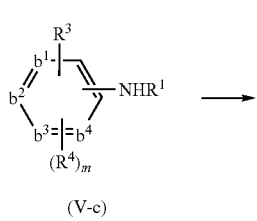

(V-c)

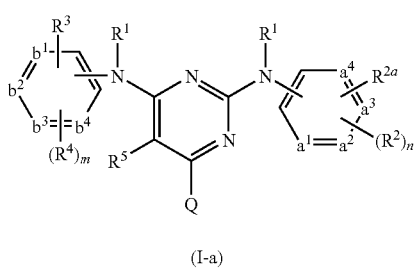

(I-a)

This conversion is also suited in the instance where $X_1$ is —O— or —S—. In particular, compounds of formula (I) wherein $X_1$ represents O, said compounds being represented by formula (I-b), can be prepared by reacting an intermediate of formula (VI) wherein $W_1$ represents a suitable leaving group, such as for example halo, e.g. chloro and the like, with an intermediate of formula (VII) in the presence of a suitable base, such as for example $K_2CO_3$ or potassium t-butoxide (KO t-Bu), and a suitable solvent, such as for example acetone or tetrahydrofuran. In a particular execution, intermediate (VII) is first reacted under stirring at room temperature with a suitable metal hydride in an organic solvent. Subsequently, an intermediate (VI), wherein —$W_1$ is a suitable leaving group, is added.

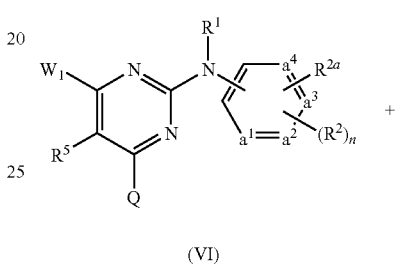

(VI)

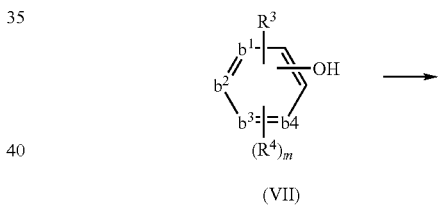

(VII)

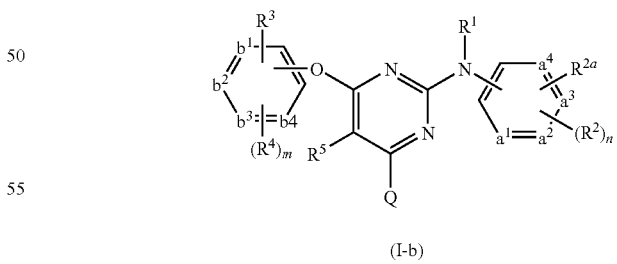

(I-b)

Compounds of formula (I-b) can also be prepared by reacting an intermediate of formula (IV-b) wherein —$X^1H$ is —OH, said intermediates being represented by (IV-d), with an intermediate of formula (VII) in the presence of $POCl_3$, a suitable base, such as for example $K_2CO_3$ or potassium t-butoxide (KO t-Bu), and a suitable solvent, such as for example acetone or tetrahydrofuran.

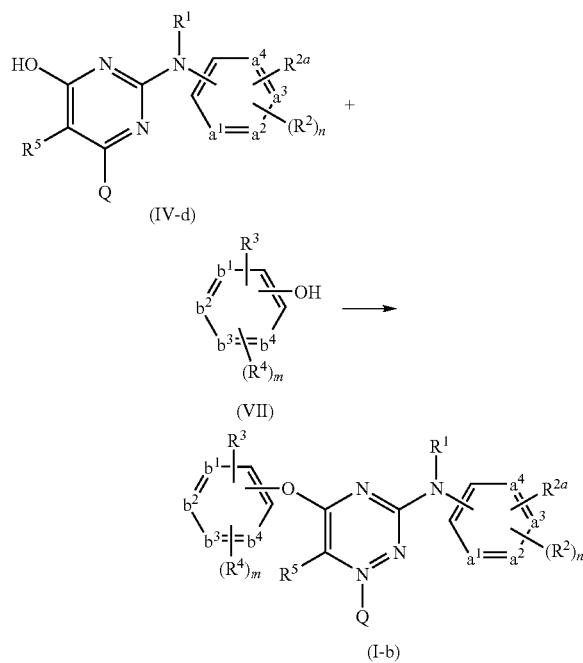

(IV-d)

(VII)

(I-b)

The thio-compounds ($X_1$ is —S—) can be obtained in a similar manner and can conveniently be transferred to the corresponding sulfoxide or sulfone using art-known oxidation procedures.

Compounds of formula (I) wherein $X_1$ is other than a heteroatom can be prepared by reacting (IV-a) with (V-a) or (IV-b) with (V-b), as outlined in the above scheme, by selecting the appropriate functional groups —$X_1$H and —$W_2$.

In particular, where $X_1$ is —C(=O)— a starting material (V-a) or (IV-b) wherein the group —$X_1$H is a Grignard type of group (—Mg-halo) or lithium is reacted with a starting material (IV-a) or (V-a) wherein $W_2$ is an ester (—COOalkyl). The latter ester may also be reduced to an alcohol with e.g. $LiAlH_4$ and subsequently oxidized with a mild oxidant such as $MnO_2$ to the corresponding aldehyde which subsequently is reacted with the appropriate starting material wherein the group —$X_1$H is a Grignard type of group (—Mg-halo) or lithium. The compounds wherein —$X_1$— is —C(=O)— can be converted to the —CHOH— analogs by a suitable reduction reaction e.g. with $LiAlH_4$.

Where $X_1$ is —$CH_2$— this linkage can be introduced by a Grignard reaction, e.g. by reacting a starting material (V-a) or (IV-b) wherein the —$X_1$H group is —$CH_2$—Mg-halo with an intermediate (IV-a) or (V-b) wherein $W_2$ is a halo group. The methylene group can be oxidized to a —C(=O)— group ($X_1$ is —C(=O)—) e.g. with selenium dioxide. The —C(=O)— group in turn can be reduced with a suitable hydride such as $LiAlH_4$ to a —CHOH— group.

The compounds of formula (I) wherein R is a radical —$Y^1$—$C_pH_{2p}$-L, wherein $Y^1$ is O, S or $NR^1$, said intermediates being represented by formula (I-c) can also be prepared by reacting an intermediate (VIII-a) wherein $W_1$ represents a suitable leaving group, such as for example halogen, e.g. chloro, bromo, with a reagent $HY^1$—$C_pH_{2p}$-L. The compounds (1-c) can also be prepared by reacting an intermediate (VIII-b) with a reagent $W_1$—$C_pH_{2p}$-L.

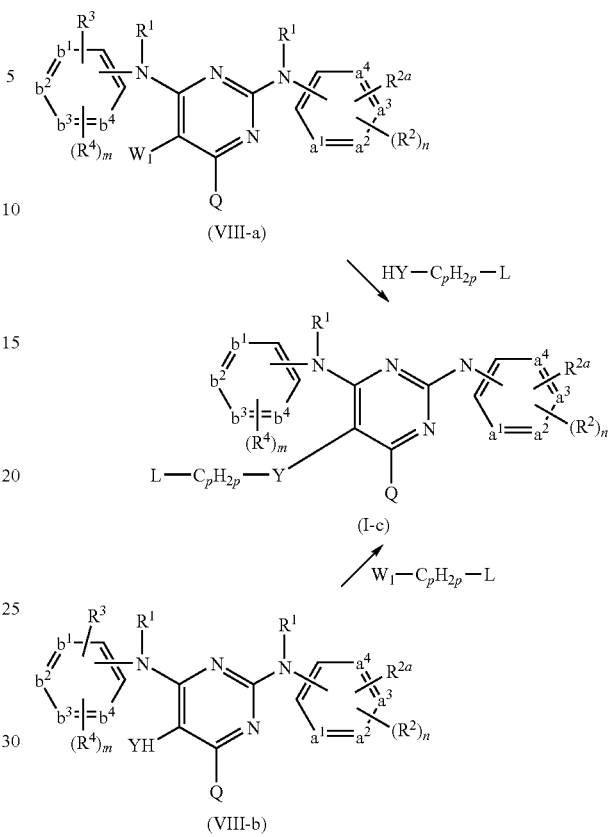

(VIII-a)

(I-c)

(VIII-b)

The compounds of formula (I-d) which are compounds of formula (I-c) wherein $Y^1$ is NH can also be prepared by a reductive amination reaction of an intermediate (VIII-a) wherein Y is NH, hereafter represented by (VIII-a-1) with a reagent O=CH—$C_{p-1}H_{2p-1}$-L. This reaction is done in a suitable solvent in the presence of a reducing agents such as hydrogen in the presence of a noble metal catalyst (e.g. Pd) or an metal hydride, e.g. sodium cyanoborohydride.

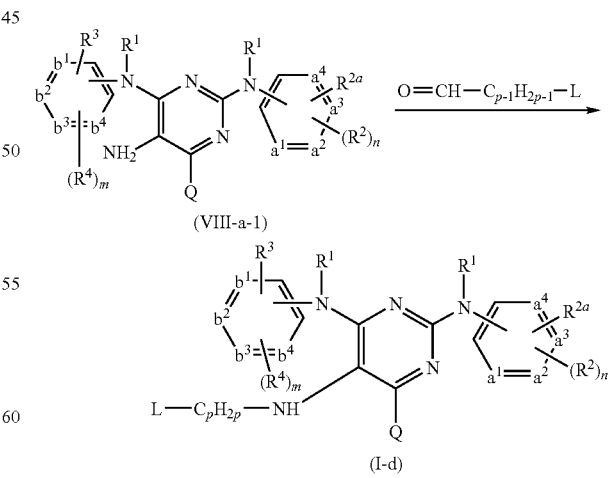

(VIII-a-1)

(I-d)

The intermediates (VIII-a) can be prepared by halogenating a corresponding starting material (IX). Other leaving groups can be introduced by replacing the halo group using suitable reagents.

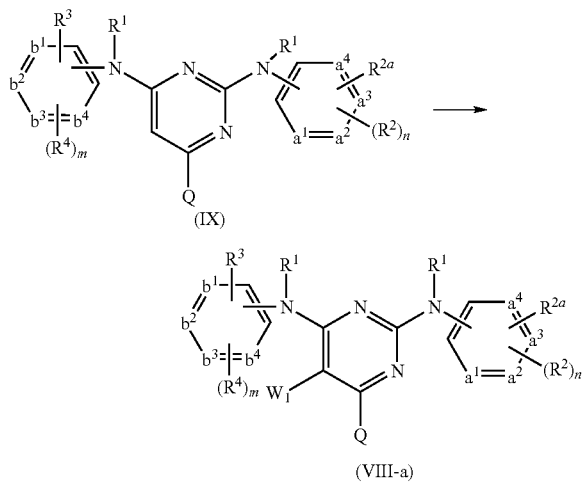

(IX)

(VIII-a)

The compounds of formula (I) wherein $R^5$ is a radical $-C_qH_{2q}-Y-C_pH_{2p}-L$, said compounds being represented by formula (I-e), can also be prepared by reacting an intermediate (X-a) wherein $W_1$ represents a suitable leaving group, such as for example halogen, e.g. chloro, bromo, with a reagent $HY-C_pH_{2p}-L$. The compounds (1-e) can also be prepared by reacting an intermediate (X-b) with a reagent $W_1-C_pH_{2p}-L$.

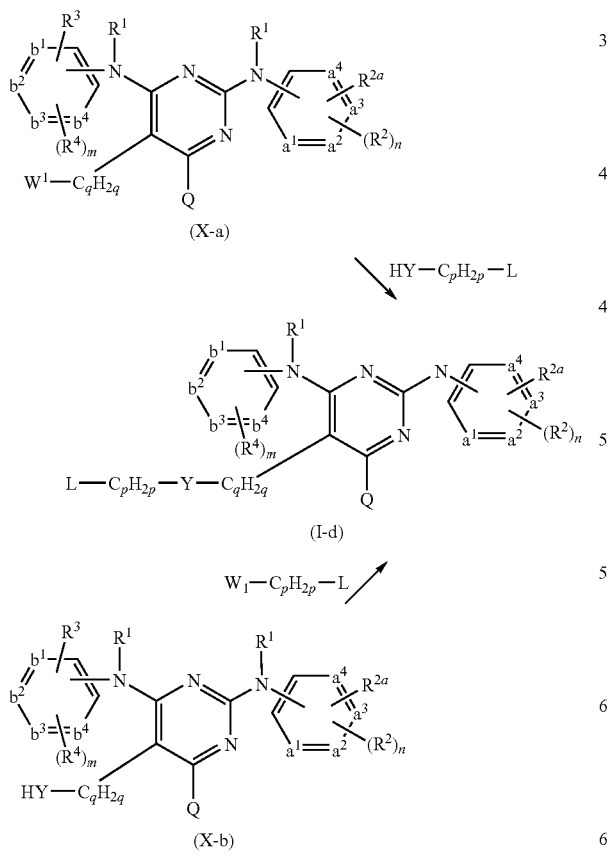

(X-a)

(I-d)

(X-b)

The compounds of formula (I-e), which are compounds of formula (I-d) wherein Y is NH, can also be prepared by a reductive amination reaction of an intermediate (X-c) with a reagent

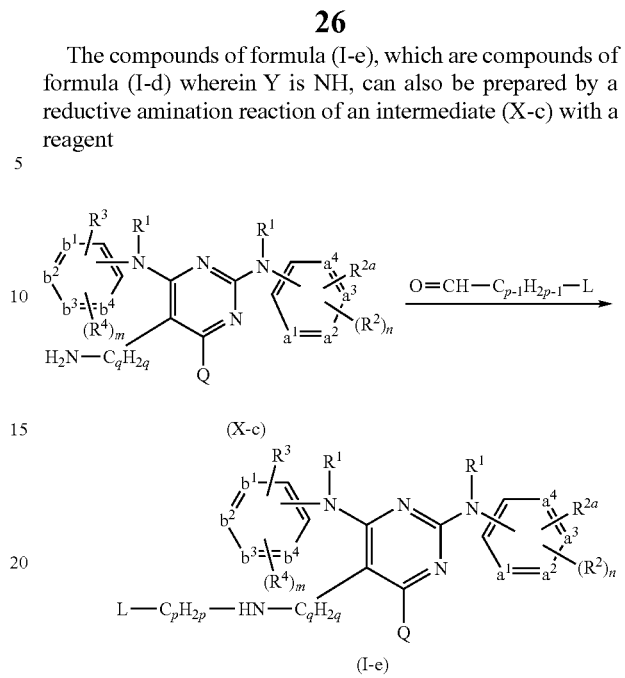

(X-c)

(I-e)

The intermediates (X-b) or (X-c) can be prepared by reacting a corresponding starting material (X-a) with as suitable nucleophile such as ammonia, an amine, a metal hydroxide or sulfhydride.

The compounds of formula (I) wherein $R^5$ is a radical $-Y-C_pH_{2p}-L$, wherein Y is $-CH=N-O-$, said compounds being represented by formula (I-f), can be prepared by reacting an intermediate (VIII-a) wherein $W_1$ represents a suitable leaving group, preferably halogen, e.g. chloro, bromo, with carbon monoxide in the presence of a suitable catalyst such as dichlorobis(triphenylphosphine)palladium (II). The resulting aldehyde (VIII-c) is reacted with a reagent $W_2-C_pH_{2p}-L$, wherein $W_2$ represents a suitable leaving group, preferably halogen, e.g. chloro, bromo, yielding the desired compounds of formula (I-f).

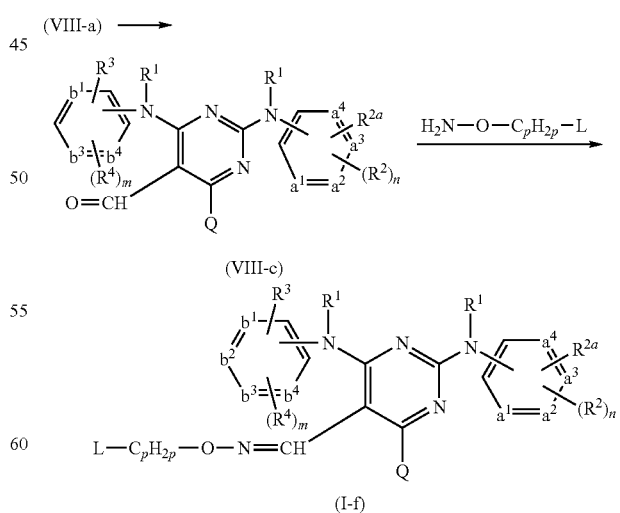

(VIII-c)

(I-f)

The compounds of formula (I) may further be prepared by converting compounds of formula (I) into each other according to art-known group transformation reactions.

The compounds of formula (I) may be converted to the corresponding N-oxide forms following art-known procedures for converting a tertiary nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert. butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein $R^1$, $R^{2a}$, $R^3$ or $R^4$ is $C_{2-6}$alkenyl substituted with aminocarbonyl, can be converted into a compound of formula (I) wherein $R^2$, $R^{2a}$, $R^3$ or $R^4$ is $C_{2-6}$alkenyl substituted with cyano by reaction with $POCl_3$.

Compounds of formula (I) wherein m is zero, can be converted into a compound of formula (I) wherein m is other than zero and $R^4$ represents halo, by reaction with a suitable halo-introducing agent, such as for example N-chlorosuccinimide or N-borosuccinimide, or a combination thereof, in the presence of a suitable solvent, such as for example acetic acid.

Compounds of formula (I) wherein $R^3$ represents halo, may be converted into a compound of formula (I) wherein $R^3$ represents $C_{2-6}$alkenyl substituted with one or more substituents each independently selected from halo, cyano, $NR^9R^{10}$, —C(=O)—$NR^9R^{10}$, —C(=O)—$C_{1-6}$alkyl or $R^7$, by reaction with the corresponding $C_{2-6}$alkene substituted with one or more substituents each independently selected from halo, cyano, $NR^9R^{10}$, —C(=O)—$NR^9R^{10}$, —C(=O)—$C_{1-6}$alkyl or $R^7$ in the presence of a suitable base, such as for example N,N-diethyl-ethanamine, a suitable catalyst, such as for example palladium acetate in the presence of triphenylphosphine, and a suitable solvent, such as for example N,N-dimethylformamide.

Compounds of formula (I) wherein $R^{2a}$ represents halo, may be converted into a compound of formula (I) wherein $R^{2a}$ represents $C_{2-6}$alkenyl substituted with one or more substituents each independently selected from halo, cyano, $NR^9R^{10}$, —C(=O)—$NR^9R^{10}$, —C(=O)—$C_{1-6}$alkyl or $R^7$, by reaction with the corresponding $C_{2-6}$alkene substituted with one or more substituents each independently selected from halo, cyano, $NR^9R^{10}$, —C(=O)—$NR^9R^{10}$, —C(=O)—$C_{1-6}$alkyl or $R^7$ in the presence of a suitable base, such as for example N,N-diethyl-ethanamine, a suitable catalyst, such as for example palladium acetate in the presence of triphenylphosphine, and a suitable solvent, such as for example N,N-dimethylformamide.

Compounds of formula (I) wherein $R^1$ represents $C_{1-6}$alkyloxycarbonyl, can be converted into a compound of formula (I) wherein $R^1$ represents hydrogen, by reaction with a suitable base, such as for example sodium hydroxide or methoxide. Where $R^1$ is t.butyloxycarbonyl, the corresponding compounds wherein $R^1$ is hydrogen can be made by treatment with trifluoroacetic acid.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials are known compounds and may be commercially available or may be prepared according to art-known procedures.

Intermediates of formula (II) can be prepared by reacting an intermediate of formula (XI) wherein $W_1$ is defined as hereinabove, with an intermediate of formula (XII) in the presence of a suitable solvent, such as for example tetrahydrofuran, and optionally in the presence of a suitable base, such as for example $Na_2CO_3$.

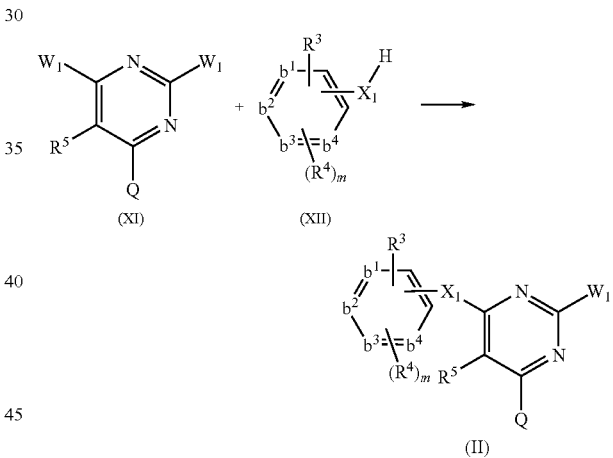

Intermediates of formula (XI) can be prepared in accordance with art-known procedures.

Intermediates of formula (III) wherein $R^1$ is hydrogen, said intermediates being represented by formula (III-a), or intermediates (V-a-1), which are intermediates (V-a) wherein —$X^1$H is —$NH_2$, can be prepared by reacting an intermediate of formula (XIII) or (XIV) with a suitable reducing agent, such as Fe, in the presence of $NH_4Cl$ and a suitable solvent, such as for example tetrahydrofuran, $H_2O$ and an alcohol, e.g. methanol and the like.

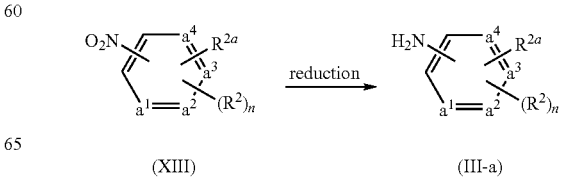

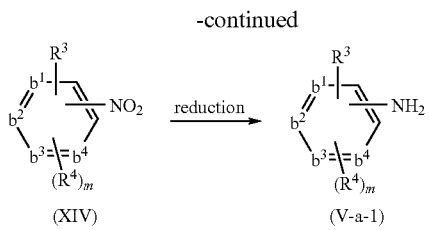

Intermediates of formula (III-a) or (V-a-1) wherein $R^{2a}$ respectively $R^3$ represents $C_{2-6}$alkyl substituted with cyano, said intermediates being represented by formula (III-a-1) and (V-a-2), can be prepared by reacting an intermediate of formula (XIII-a) respectively (XIV-a) with Pd/C in the presence of a suitable solvent, such as for example an alcohol, e.g. ethanol and the like.

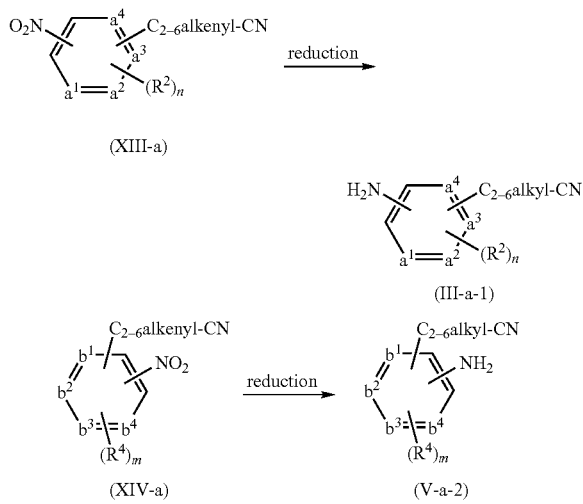

Intermediates of formula (III), (V-a) or (VII) wherein $R^{2a}$ respectively $R^3$ is halo, said intermediates being represented by formula (III-b), (V-b) and (VII-a), may be converted into an intermediate of formula (III) respectively (V) or (VII) wherein $R^{2a}$ respectively $R^3$ is $C_{2-6}$alkenyl substituted with $C(=O)NR^9R^{10}$, said intermediates being represented by formula (III-c), (V-c) and (VII-b) by reaction with an intermediate of formula (XIII) in the presence of Pd(OAc)$_2$, P(o-Tol)$_3$, a suitable base, such as for example N,N-diethylethanamine, and a suitable solvent, such as for example CH$_3$—CN.

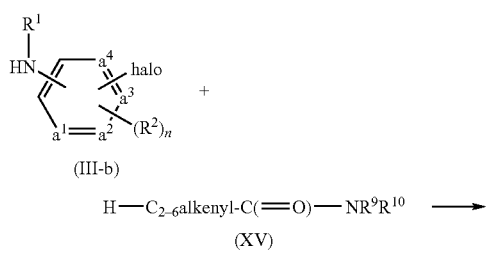

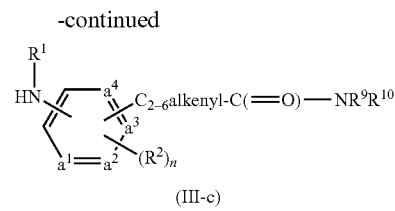

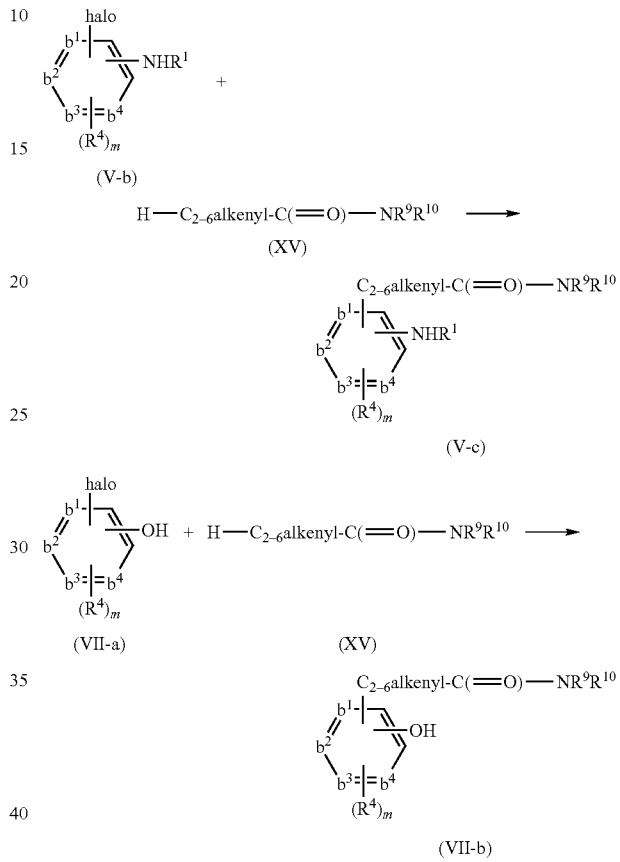

Intermediates of formula (III-c), (V-c) and (VII-b) can also be prepared by reacting an intermediate of formula (II-f), (V-f) and (VII-c) with H—NR$^9$R$^{10}$ in the presence of oxalyl chloride and in the presence of a suitable solvent, such as for example N,N-dimethylformamide, CH$_2$Cl$_2$ and tetrahydrofuran.

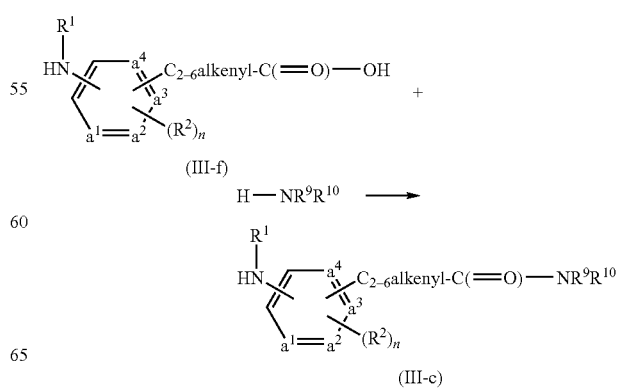

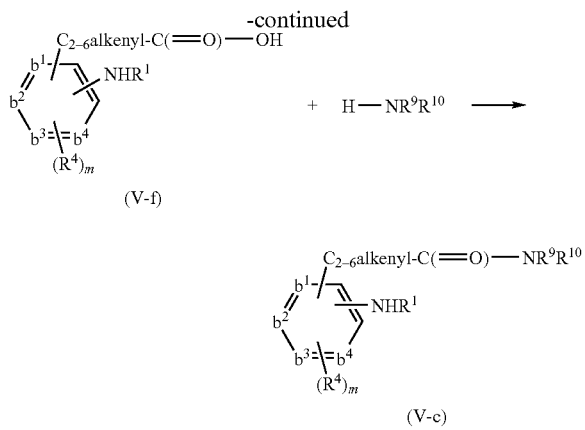

Intermediates of formula (III-d), (V-d) and (VII-c) can be prepared by reacting an intermediate of formula (III-b), (V-b) and (VII-a), with H—C$_{2-6}$alkenyl-C(=O)—OH in the presence of Pd(OAc)$_2$, P(o-Tol)$_3$, a suitable base, such as for example N,N-diethylethanamine, and a suitable solvent, such as for example CH$_3$—CN.

Intermediates of formula (III-b), (V-b) and (VII-a), may also be converted into an intermediate of formula (III) respectively (V) or (VII) wherein R$^{21}$ respectively R$^3$ is C$_{2-6}$alkenyl substituted with CN, said intermediates being represented by formula (III-e), (V-e) and (VII-d) by reaction with H—C$_{2-6}$alkenyl-CN in the presence of Pd(OAc)$_2$, P(o-Tol)$_3$, a suitable base, such as for example N,N-diethylethanamine, and a suitable solvent, such as for example CH$_3$—CN.

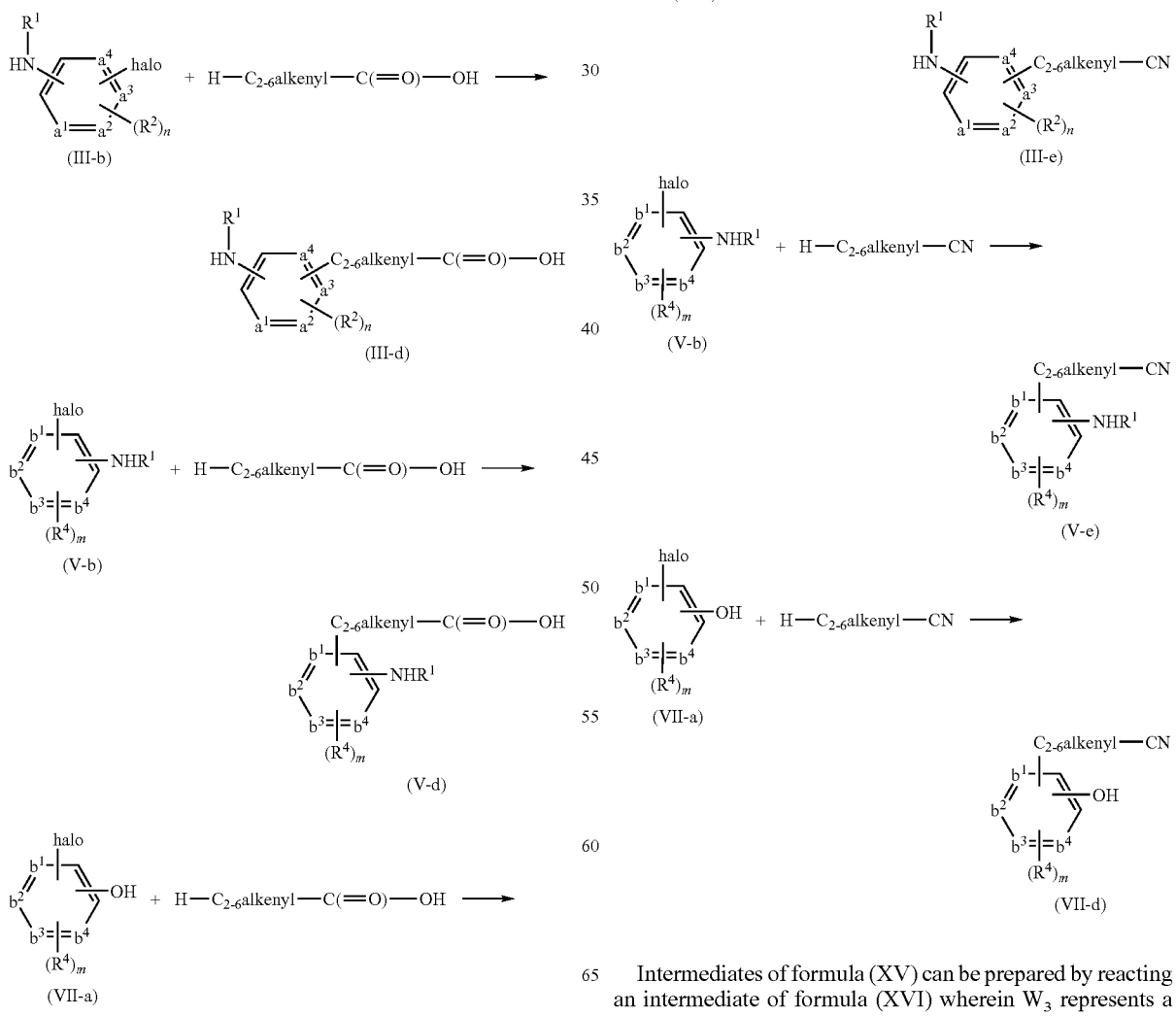

Intermediates of formula (XV) can be prepared by reacting an intermediate of formula (XVI) wherein W$_3$ represents a suitable leaving group, such as for example halogen, e.g.

chloro, with H—NR$^9$R$^{10}$ (XVII) in the presence of a suitable solvent, such as for example diethylether and tetrahydrofuran.

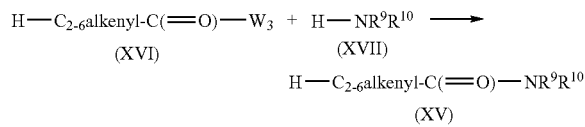

Intermediates of formula (XIII) or (XIV) wherein R$^{2a}$ respectively R$^3$ represents cyanovinyl, said intermediates being represented by formula (XIII-b) and (XIV-b), can be prepared by reacting an intermediate of formula (XVIII) respectively (XIX) with diethylcyanomethylphosphonate in the presence of a suitable base, such as for example NaOCH$_3$, and a suitable solvent, such as for example tetrahydrofuran.

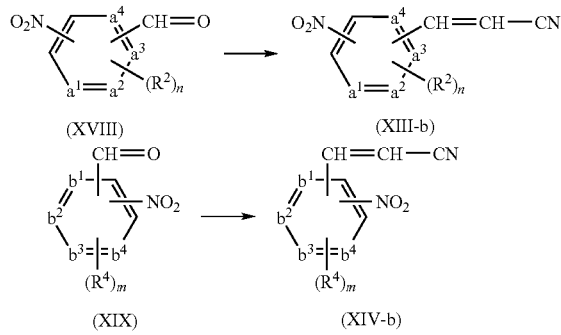

Intermediates of formula (XIII) or (XIV) wherein R$^{2a}$ respectively R$^3$ represents —C(CH$_3$)═CH—CN, said intermediates being represented by formula (XIII-c) and (XIII-c), can be prepared by reacting an intermediate of formula (XX) respectively (XXI) with diethylcyanomethylphosphonate in the presence of a suitable base, such as for example NaOCH$_3$, and a suitable solvent, such as for example tetrahydrofuran.

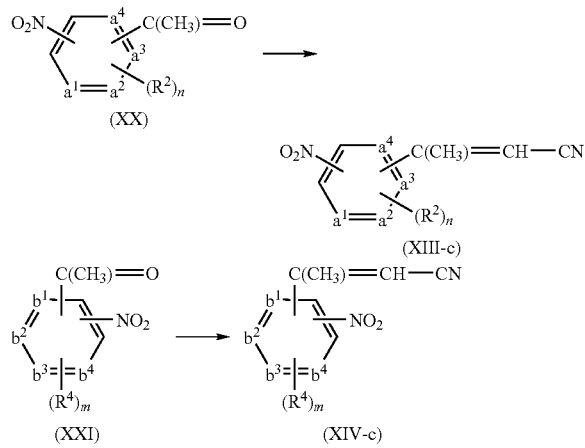

Intermediates of formula (XVIII) and (XIX) can be prepared by reacting an intermediate of formula (XXII) respectively (XXIII) with a suitable oxidizing agent, such as for example MnO$_2$, in the presence of a suitable solvent, such as for example acetone.

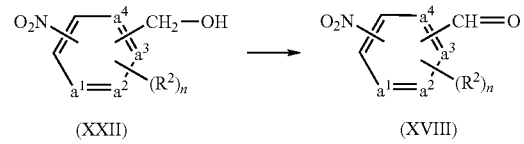

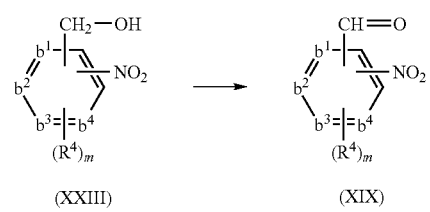

Intermediates of formula (XXII) and (XXIII) can be prepared by reacting an intermediate of formula (XXIV) respectively (XXV) with NaBH$_4$ in the presence of ethylchloroformate, a suitable base, such as for example N,N-diethylethanamine, and a suitable solvent, such as for example tetrahydrofuran.

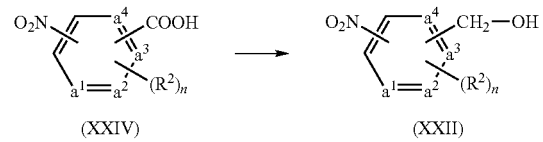

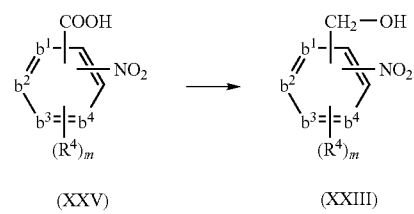

Intermediates of formula (XIII) and (XIV) wherein R$^{2a}$ respectively R$^3$ represent hydroxy, said intermediates being represented by formula (XIII-d) respectively (XIV-d), can be converted into an intermediate of formula (XIII) respectively (XIV) wherein R$^{2a}$ respectively R$^3$ represent C$_{1-6}$alkyloxy wherein the C$_{1-6}$alkyl may optionally be substituted with cyano, said R$^{2a}$ respectively R$^3$ being represented by P and said intermediates being represented by formula (XIII-e) respectively (XIV-e), by reaction with an intermediate of formula (XXV) wherein W$_4$ represents a suitable leaving group, such as for example halogen, e.g. chloro and the like, in the presence of NaI, a suitable base, such as for example K$_2$CO$_3$, and a suitable solvent, such as for example acetone.

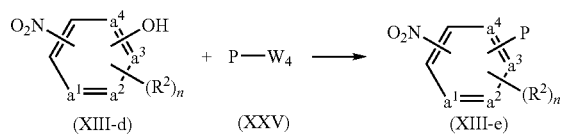

-continued

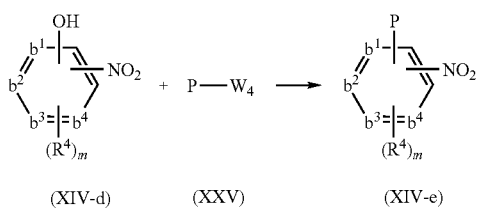

(XIV-d)   (XXV)   (XIV-e)

Intermediates of formula (XIII) and (XIV) can be prepared by reacting an intermediate of formula (XXVI) respectively (XXVII) with $NaNO_3$ in the presence of $CH_3SO_3H$.

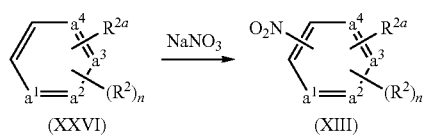

(XXVI)   (XIII)

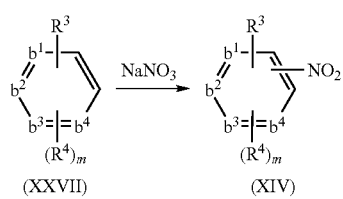

(XXVII)   (XIV)

The intermediates of formula (IV-d) can be prepared as follows

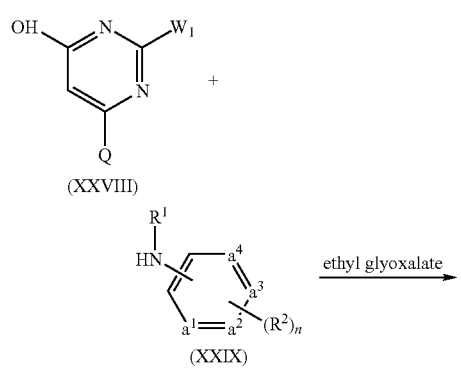

(XXVIII)

(XXIX)

(IV-d)

Intermediates of formula (XXX) can be converted into intermediates of formula (IV-e) which are intermediates of formula (IV-d) wherein $R^5$ represents bromo by reaction with $Br_2$ in the presence of a suitable base, such as for example N,N-diethylethanamine, and a suitable solvent, such as for example dimethylsulfoxide.

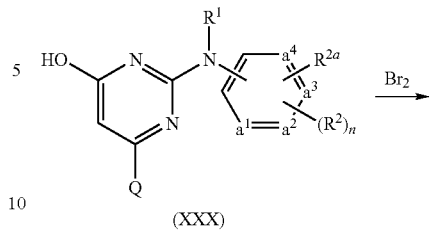

(XXX)

(IV-e)

Intermediates of formula (IV-e) can be converted into intermediates of formula (VI) wherein $R^5$ and $W_2$ represent chloro, said intermediate being represented by formula (VI-a), by reaction with $POCl_3$.

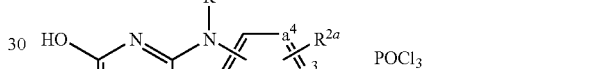

(IV-a)

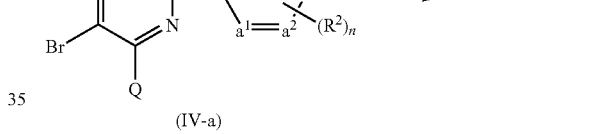

(VI-a)

The compounds of formula (I) show antiretroviral properties (reverse transcriptase inhibiting properties), in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an ever decreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against (multi) drug resistant HIV strains, in particular (multi) drug resistant HIV-1 strains, more in particular the present compounds show activity against HIV strains, especially HIV-1 strains, that have acquired resistance to one or more art-known non-nucleoside reverse transcriptase inhibitors. Art-known non-nucleoside reverse transcriptase inhibitors are those non-nucleoside reverse transcriptase inhibitors other than the present compounds and known to the person skilled in the art, in particular commercial non-nucleoside reverse transcriptase inhibitors. The present compounds also have little or no binding affinity to human α-1 acid glycoprotein; human α-1 acid glycoprotein does not or only weakly affect the anti HIV activity of the present compounds.

Due to their antiretroviral properties, particularly their anti-HIV properties, especially their anti-HIV-1-activity, the compounds of formula (I), their N-oxides, pharmaceutically acceptable addition salts, quaternary amines and stereochemically isomeric forms thereof, are useful in the treatment of individuals infected by HIV and for the prophylaxis of these infections. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic Central Nervous System diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the administration to HIV-infected subjects of an amount effective to combat the conditions associated with HIV and other pathogenic retroviruses, especially HIV-1. In particular, the compounds of formula (I) may be used in the manufacture of a medicament for the treatment or the prevention of HIV infections.

In view of the utility of the compounds of formula (I), there is provided a method of treating warm-blooded animals, including humans, suffering from or a method of preventing warm-blooded animals, including humans, to suffer from viral infections, especially HIV infections. Said method comprises the administration, preferably oral administration, of an effective amount of a compound of formula (I), a N-oxide form, a pharmaceutically acceptable addition salt, a quaternary amine or a possible stereoisomeric form thereof, to warm-blooded animals, including humans.

The present invention also provides compositions for treating viral infections comprising a therapeutically effective amount of a compound of formula (I) and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

To aid solubility of the compounds of formula (I), suitable ingredients, e.g. cyclodextrins, may be included in the compositions. Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxy-propyl or hydroxybutyl; carboxy$C_{1-6}$alkyl, particularly carboxymethyl or carboxy-ethyl; $C_{1-6}$alkylcarbonyl, particularly acetyl. Especially noteworthy as complexants and/or solubilizers are β-CD, randomly methylated β-CD, 2,6-dimethyl-β-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The average substitution degree (D.S.) refers to the average number of substituted hydroxyls per anhydroglucose unit. The M.S. and D.S. value can be determined by various analytical techniques such as nuclear magnetic resonance (NMR), mass spectrometry (MS) and infrared spectroscopy (IR). Depending on the technique used, slightly different values may be obtained for one given cyclodextrin derivative. Preferably, as measured by mass spectrometry, the M.S. ranges from 0.125 to 10 and the D.S. ranges from 0.125 to 3.

Other suitable compositions for oral or rectal administration comprise particles consisting of a solid dispersion comprising a compound of formula (I) and one or more appropriate pharmaceutically acceptable water-soluble polymers.

The term "a solid dispersion" used hereinafter defines a system in a solid state (as opposed to a liquid or gaseous state) comprising at least two components, in casu the compound of formula (I) and the water-soluble polymer, wherein one component is dispersed more or less evenly throughout the other component or components (in case additional pharmaceutically acceptable formulating agents, generally known in the art, are included, such as plasticizers, preservatives and the like). When said dispersion of the components is such that the system is chemically and physically uniform or homogenous throughout or consists of one phase as defined in thermodynamics, such a solid dispersion will be called "a solid solution". Solid solutions are preferred physical systems because the components therein are usually readily bioavailable to the organisms to which they are administered. This advantage can probably be explained by the ease with which said solid solutions can form liquid solutions when contacted with a liquid medium such as the gastrointestinal juices. The ease of dissolution may be attributed at least in part to the fact that the energy required for dissolution of the components from a solid solution is less than that required for the dissolution of components from a crystalline or microcrystalline solid phase.

The term "a solid dispersion" also comprises dispersions, which are less homogenous throughout than solid solutions. Such dispersions are not chemically and physically uniform throughout or comprise more than one phase. For example, the term "a solid dispersion" also relates to a system having domains or small regions wherein amorphous, microcrystalline or crystalline compound of formula (I), or amorphous, microcrystalline or crystalline water-soluble polymer, or both, are dispersed more or less evenly in another phase comprising water-soluble polymer, or compound of formula (I), or a solid solution comprising compound of formula (I) and water-soluble polymer. Said domains are regions within the solid dispersion distinctively marked by some physical feature, small in size, and evenly and randomly distributed throughout the solid dispersion.

Various techniques exist for preparing solid dispersions including melt-extrusion, spray-drying and solution-evaporation.

The solution-evaporation process comprises the following steps
a) dissolving the compound of formula (I) and the water-soluble polymer in an appropriate solvent, optionally at elevated temperatures;
b) heating the solution resulting under point a), optionally under vacuum, until the solvent is evaporated. The solution may also be poured onto a large surface so as to form a thin film, and evaporating the solvent therefrom.

In the spray-drying technique, the two components are also dissolved in an appropriate solvent and the resulting solution is then sprayed through the nozzle of a spray dryer followed by evaporating the solvent from the resulting droplets at elevated temperatures.

The preferred technique for preparing solid dispersions is the melt-extrusion process comprising the following steps:
a) mixing a compound of formula (I) and an appropriate water-soluble polymer,
b) optionally blending additives with the thus obtained mixture,
c) heating and compounding the thus obtained blend until one obtains a homogenous melt,
d) forcing the thus obtained melt through one or more nozzles; and
e) cooling the melt until it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products can be optionally milled and sieved.

The solid dispersion product may be milled or ground to particles having a particle size of less than 600 μm, preferably less than 400 μm and most preferably less than 125 μm.

The particles prepared as described hereinabove can then be formulated by conventional techniques into pharmaceutical dosage forms such as tablets and capsules.

It will be appreciated that a person of skill in the art will be able to optimize the parameters of the solid dispersion preparation techniques described above, such as the most appropriate solvent, the working temperature, the kind of apparatus being used, the rate of spray-drying, the throughput rate in the melt-extruder.

The water-soluble polymers in the particles are polymers that have an apparent viscosity, when dissolved at 20° C. in an aqueous solution at 2% (w/v), of 1 to 5000 mPa.s more preferably of 1 to 700 mPa.s, and most preferred of 1 to 100 mPa.s. For example, suitable water-soluble polymers include alkylcelluloses, hydroxyalkylcelluloses, hydroxyalkyl alkylcelluloses, carboxyalkylcelluloses, alkali metal salts of carboxyalkylcelluloses, carboxyalkylalkylcelluloses, carboxyalkylcellulose esters, starches, pectines, chitin derivates, di-, oligo- and polysaccharides such as trehalose, alginic acid or alkali metal and ammonium salts thereof, carrageenans, galactomannans, tragacanth, agar-agar, gummi arabicum, guar gummi and xanthan gummi, polyacrylic acids and the salts thereof, polymethacrylic acids and the salts thereof, methacrylate copolymers, polyvinylalcohol, polyvinylpyrrolidone, copolymers of polyvinylpyrrolidone with vinyl acetate, combinations of polyvinylalcohol and polyvinylpyrrolidone, polyalkylene oxides and copolymers of ethylene oxide and propylene oxide. Preferred water-soluble polymers are hydroxypropyl methylcelluloses. Also one or more cyclodextrins can be used as water-soluble polymer in the preparation of the above-mentioned particles as is disclosed in WO 97/18839. Said cyclodextrins include the pharmaceutically acceptable unsubstituted and substituted cyclodextrins known in the art, more particularly α, β or γ cyclodextrins or the pharmaceutically acceptable derivatives thereof.

Substituted cyclodextrins which can be used to prepare the above described particles include polyethers described in U.S. Pat. No. 3,459,731. Further substituted cyclodextrins are ethers wherein the hydrogen of one or more cyclodextrin hydroxy groups is replaced by $C_{1-6}$alkyl, hydroxy $C_{1-6}$alkyl, carboxy-$C_{1-6}$alkyl or $C_{1-6}$alkyloxycarbonyl-$C_{1-6}$alkyl or mixed ethers thereof. In particular such substituted cyclodextrins are ethers wherein the hydrogen of one or more cyclodextrin hydroxy groups is replaced by $C_{1-3}$alkyl, hydroxy$C_{2-4}$ alkyl or carboxyC$_{1-2}$alkyl or more in particular by methyl, ethyl, hydroxyethyl, hydroxypropyl, hydroxybutyl, carboxymethyl or carboxyethyl.

Of particular utility are the β-cyclodextrin ethers, e.g. dimethyl-β-cyclodextrin as described in Drugs of the Future, Vol. 9, No. 8, p. 577-578 by M. Nogradi (1984) and polyethers, e.g. hydroxypropyl β-cyclodextrin and hydroxyethyl β-cyclodextrin, being examples. Such an alkyl ether may be a methyl ether with a degree of substitution of about 0.125 to 3, e.g. about 0.3 to 2. Such a hydroxypropyl cyclodextrin may for example be formed from the reaction between β-cyclodextrin an propylene oxide and may have a MS value of about 0.125 to 10, e.g. about 0.3 to 3.

Another type of substituted cyclodextrins is sulfobutylcyclodextrines.

The ratio of the compound of formula (I) over the water soluble polymer may vary widely. For example ratios of 1/100 to 100/1 may be applied. Interesting ratios of the compound of formula (I) over cyclodextrin range from about 1/10 to 10/1. More interesting ratios range from about 1/5 to 5/1.

It may further be convenient to formulate the compounds of formula (I) in the form of nanoparticles which have a surface modifier adsorbed on the surface thereof in an amount sufficient to maintain an effective average particle size of less than 1000 nm. Useful surface modifiers are believed to include those which physically adhere to the surface of the compound of formula (I) but do not chemically bond to said compound.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds of formula (I) involves a pharmaceutical composition whereby the compounds of formula (I) are incorporated in hydrophilic polymers and applying this mixture as a coat film over many small beads, thus yielding a composition which can conveniently be manufactured and which is suitable for preparing pharmaceutical dosage forms for oral administration.

Said beads comprise a central, rounded or spherical core, a coating film of a hydrophilic polymer and a compound of formula (I) and optionally a seal-coating layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

The present compounds of formula (I) can be used alone or in combination with other therapeutic agents, such as antivirals, antibiotics, immunomodulators or vaccines for the treatment of viral infections. They may also be used alone or in combination with other prophylacetic agents for the prevention of viral infections. The present compounds may be used in vaccines and methods for protecting individuals against viral infections over an extended period of time. The compounds may be employed in such vaccines either alone or together with other compounds of this invention or together with other anti-viral agents in a manner consistent with the conventional utilization of reverse transcriptase inhibitors in vaccines. Thus, the present compounds may be combined with pharmaceutically acceptable adjuvants conventionally employed in vaccines and administered in prophylactically effective amounts to protect individuals over an extended period of time against HIV infection.

Also, the combination of one or more additional antiretroviral compounds and a compound of formula (I) can be used as a medicine. Thus, the present invention also relates to a product containing (a) a compound of formula (I), and (b) one or more additional antiretroviral compounds, as a combined preparation for simultaneous, separate or sequential use in anti-HIV treatment. The different drugs may be combined in a single preparation together with pharmaceutically acceptable carriers. Said other antiretroviral compounds may be any known antiretroviral compounds such as suramine, pentamidine, thymopentin, castanospermine, dextran (dextran sulfate), foscarnet-sodium (trisodium phosphono formate); nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), D-D4FC (Reverset™), alovudine (MIV-310), amdoxovir (DAPD), elvucitabine (ACH-126,443), and the like; non-nucleoside reverse transcriptase inhibitors (NNRTIs) such as delarvidine (DLV), efavirenz (EFV), nevirapine (NVP), capravirine (CPV), calanolide A, TMC120, etravirine (TMC125), TMC278, BMS-561390, DPC-083 and the like; nucleotide reverse transcriptase inhibitors (NtRTIs), e.g. tenofovir (TDF) and tenofovir disoproxil fumarate, and the like; compounds of the TIBO (tetrahydroimidazo-[4,5,1-jk] [1,4]-benzodiazepine-2(1H)-one and thione)-type e.g. (S)-8-chloro-4,5,6,7-tetrahydro-5-methyl-6-(3-methyl-2-butenyl) imidazo-[4,5,1-jk][1,4]benzodiazepine-2(1H)-thione; compounds of the α-APA (α-anilino phenyl acetamide) type e.g. α-[(2-nitrophenyl)amino]-2,6-dichlorobenzene-acetamide and the like; inhibitors of trans-activating proteins, such as TAT-inhibitors, e.g. RO-5-3335; REV inhibitors; protease inhibitors e.g. ritonavir (RTV), saquinavir (SQV), lopinavir (ABT-378 or LPV), indinavir (IDV), amprenavir (VX-478), TMC-126, BMS-232632, VX-175, DMP-323, DMP-450 (Mozenavir), nelfinavir (AG-1343), atazanavir (BMS 232, 632), palinavir, TMC-114, RO033-4649, fosamprenavir (GW433908 or VX-175), P-1946, BMS 186,318, SC-55389a, L-756,423, tipranavir (PNU-140690), BILA 1096 BS, U-140690, and the like; entry inhibitors which comprise fusion inhibitors (e.g. T-20, T-1249), attachment inhibitors and co-receptor inhibitors; the latter comprise the CCR5 antagonists and CXR4 antagonists (e.g. AMD-3100); examples of entry inhibitors are enfuvirtide (ENF), GSK-873,140, PRO-542, SCH-417,690, TNX-355, maraviroc (UK-427,857); a maturation inhibitor for example is PA-457 (Panacos Pharmaceuticals); inhibitors of the viral integrase; ribonucleotide reductase inhibitors (cellular inhibitors), e.g. hydroxyurea and the like.

By administering the compounds of the present invention with other anti-viral agents which target different events in the viral life cycle, the therapeutic effect of these compounds can be potentiated. Combination therapies as described above exert a synergistic effect in inhibiting HIV replication because each component of the combination acts on a different site of HIV replication. The use of such combinations may reduce the dosage of a given conventional anti-retroviral agent which would be required for a desired therapeutic or prophylacetic effect as compared to when that agent is administered as a monotherapy. These combinations may reduce or eliminate the side effects of conventional single anti-retroviral therapy while not interfering with the anti-viral activity of the agents. These combinations reduce potential of resistance to single agent therapies, while minimizing any associated toxicity. These combinations may also increase the efficacy of the conventional agent without increasing the associated toxicity.

The compounds of the present invention may also be administered in combination with immunomodulating agents, e.g. levamisole, bropirimine, anti-human alpha interferon antibody, interferon alpha, interleukin 2, methionine enkephalin, diethyldithiocarbamate, tumor necrosis factor, naltrexone and the like; antibiotics, e.g. pentamidine isethiorate and the like; cholinergic agents, e.g. tacrine, rivastigmine, donepezil, galantamine and the like; NMDA channel blockers, e.g. memantine to prevent or combat infection and diseases or symptoms of diseases associated with HIV infections, such as AIDS and ARC, e.g. dementia. A compound of formula (I) can also be combined with another compound of formula (I).

Although the present invention focuses on the use of the present compounds for preventing or treating HIV infections, the present compounds may also be used as inhibitory agents for other viruses which depend on similar reverse transcriptases for obligatory events in their life cycle.

The following examples are intended to illustrate the present invention.

EXAMPLES

Hereinafter, "DMSO" is defined as dimethylsulfoxide, "TFA" is defined as trifluoroacetic acid, "DMF" is defined as N,N-dimethylformamide and "THF" is defined as tetrahydrofuran.

A. Preparation of the Intermediate Compounds

Example A1

Preparation of Intermediate 2

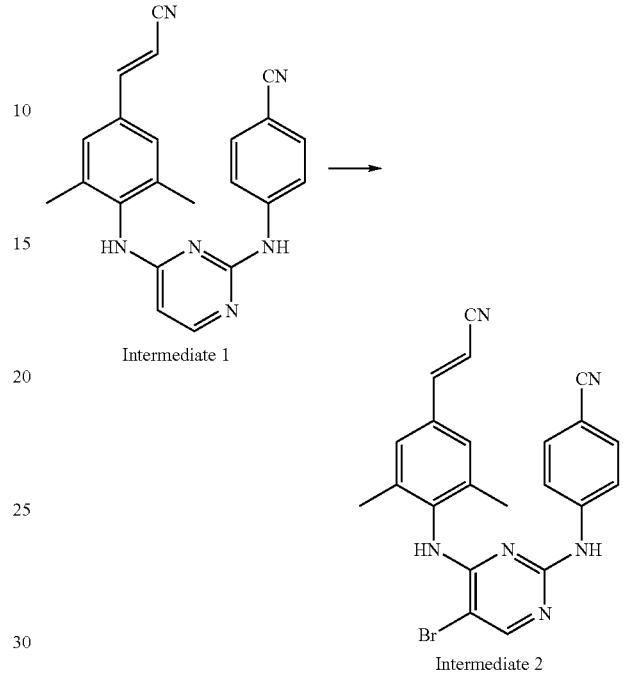

N-bromosuccinimide (0.0393 mol) was added portion wise at room temperature to Intermediate 1, the preparation of which has been described in WO-03/016306 (0.0327 mol) in $CH_3CN$ (100 ml). The mixture was stirred at room temperature for 4 hours. The precipitate was filtered off, washed with $CH_3CN$ and dried yielding 10.08 g of the desired end product. The filtrate was evaporated and purified by column chromatography (eluent: $CH_2Cl_2$ 100; 35-70 μm). The pure fractions were collected, the solvent was evaporated and the residue was crystallized from $CH_3CN$. Yielding: 2.4 g of Intermediate 2. The two fractions were collected. Yielding: 12.48 g of Intermediate 2 (86%, melting point: >250° C.).

Example A2

Preparation of Intermediate 3

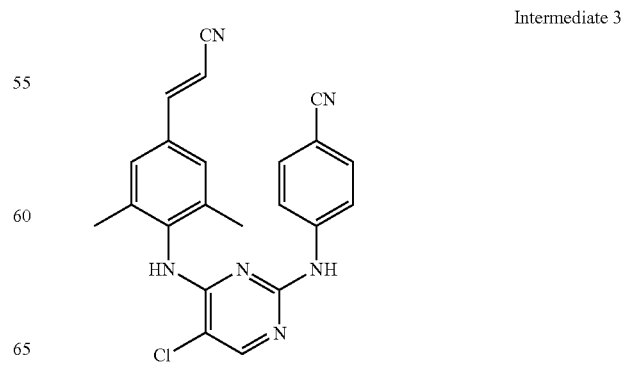

N-chlorosuccinimide (0.000327 mol) was added portion wise at room temperature to Intermediate 1 (0.000273 mol) in CH₃CN (5 ml). The mixture was stirred at room temperature for 4 hours. The precipitate was filtered, washed with CH₃CN and dried. Yielding: 0.065 g (59%, melting point: >250° C.).

Example A3

Preparation of Intermediate 4

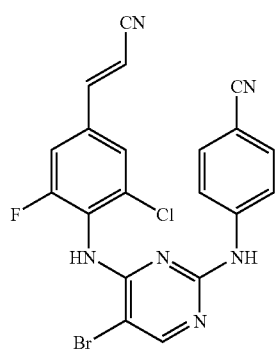

Intermediate 4

The same procedure as in example A1 was used, starting from 2-fluoro-6-chloro analog of Intermediate 1 (0.000128 mol) and N-bromosuccinimide (0.000154 mol) in CH₃CN (5 ml), yielding: 0.037 g of Intermediate 4 (62%, melting point: 236° C.)

Example A4

Preparation of Intermediates 5, 6, 7

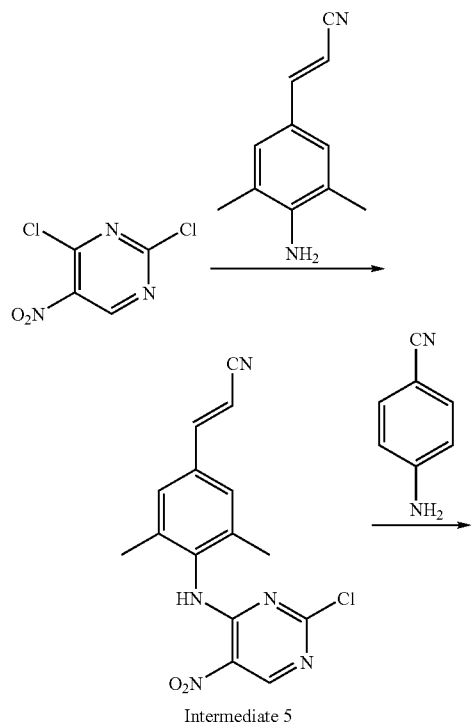

Intermediate 5

-continued

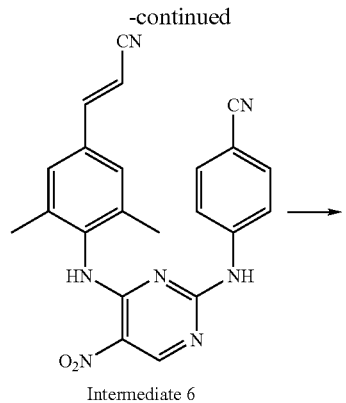

Intermediate 6

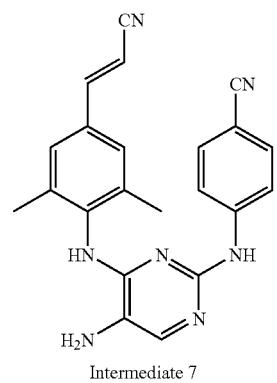

Intermediate 7

A mixture of 2,4-dichloro-5-nitro-pyrimidine (0.0516 mol) and 4-(2-cyanoethenyl)-2,6-dimethylphenylamine (0.0516 mol) were stirred at 140° C. in an oil bath for 45 minutes, then poured in a mixture of water and K₂CO₃ 10%. The precipitate was filtered and the filtrate extracted with CH₂Cl₂. The organic layer was dried over magnesium sulfate, filtered and the solvent evaporated. The residue was purified by column chromatography over silica gel (eluent: CH₂Cl₂ 100; 35-70 μm). The pure fractions were collected and the solvent evaporated, yielding: 6.0 g of Intermediate 5 (35%, melting point: >250° C.).

Preparation of Intermediate 6

A mixture of Intermediate 5 (0.0182 mol) and 4-cyanoaniline (0.0182 mol) were heated at fusion for 5 minutes, then poured in a mixture of water and K₂CO₃ 10%. CH₂Cl₂ and a small quantity of MeOH were added and the precipitate was filtered and dried. Yielding: 7.4 g of Intermediate 6 (95%, melting point: >250° C.)

Preparation of Intermediate 7

A mixture of Intermediate 6 (0.0180 mol) and tin (II) chloride dihydrate (0.125 mol) in ethanol (100 ml) were stirred at 70° C. overnight, then poured in a mixture of water and K₂CO₃ 10%. The precipitate was filtered over celite. The filtrate was removed and the precipitate washed with CH₂Cl₂ and THF. The solvent was evaporated. Yield: 6.0 g of Intermediate 7 (87%, melting point: >250° C.).

Example A5

Preparation of the 2-fluoro-6-chloro-phenyl Analogs of Intermediates 5, 6 and 7

A mixture of 2,4-dichloro-5-nitro-pyrimidine (0.0153 mol) and 4-(2-cyanoethenyl)-2-fluoro-6-chloro-phenylamine (0.0153 mol) were heated at fusion for 5 minutes, then poured in a mixture of water and K₂CO₃ 10% and extracted with CH₂Cl₂. The organic layer was dried over magnesium sulfate, filtered and the solvent evaporated. The residue was purified by column chromatography over silica gel (eluent: CH₂Cl₂ 100; 35-70 μm). The pure fractions were collected and the solvent evaporated. Yield: 1.9 g of 2-chloro-4-[4-(2-cyanoethenyl)-2-fluoro-6-chloro-phenylamino]-5-nitro-pyrimidine, Intermediate 8 (35%, melting point: 217° C.).

A mixture of Intermediate 8 (0.000424 mol) and 4-cyanoaniline (0.000424 mol) were heated at fusion for 5 minutes, then poured in a mixture of water and K₂CO₃ 10%. CH₂Cl₂ and a small quantity of MeOH were added and the precipitate was filtered and dried. Yield: 1.34 g of 4-[4-[4-(2-cyanoethenyl)-2-fluoro-6-chloro-phenylamino]-5-nitro-pyrimidine]amino]benzonitrile, Intermediate 9 (73%, melting point: >250° C.)

A mixture of Intermediate 9 (0.00306 mol) and tin (II) chloride dihydrate (0.0214 mol) in ethanol (20 ml) were stirred at 70° C. overnight, then poured in a mixture of water and K₂CO₃ 10%. The precipitate was filtered over celite. The filtrate was removed and the precipitate washed with CH₂Cl₂ and THF. The solvent was evaporated. Yield: 1.1 g of 4-[4-[4-(2-cyanoethenyl)-2-fluoro-6-chloro-phenylamino]-5-aminopyrimidine]amino]benzonitrile, Intermediate 10 (89%, melting point: >250° C.).

Example A6

Preparation of Intermediate 11

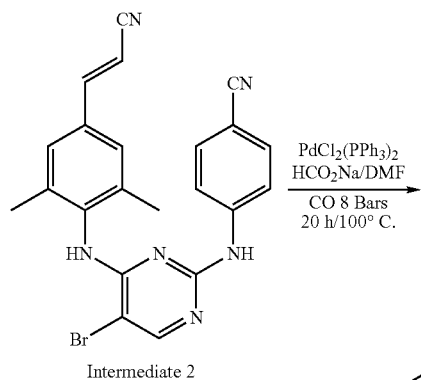

Intermediate 2

A mixture of intermediate 2 (0.0112 mol), dichlorobis(triphenylphosphine)-palladium(II) (0.00228 mol), sodium formate (0.0336 mol) and magnesium sulfate (1 g) in DMF (50 ml) were stirred at 100° C. for 20 hours under 8 bars pressure of carbon monoxide. The mixture was filtered over celite and poured in water. The precipitate was filtered off, washed with water and Et₂O and dried. Yield: 2.9 g. of intermediate 11 (65%, melting point: >250° C.).

Example A7

Preparation of Intermediate 12

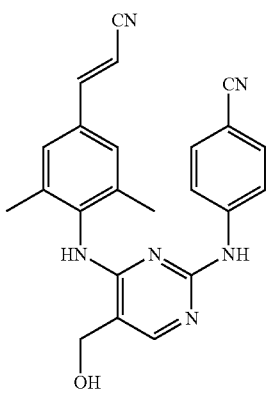

Sodium borohydride was added portionwise at 0° C. to intermediate 11 (0.000254 mol) in THF (5 ml) and EtOH (3 ml). The mixture was stirred at room temperature for 15 min. The mixture was poured in water and extracted with CH₂Cl₂. The organic layer was dried over magnesium sulfate, filtered and the solvent evaporated. The residue was crystallized from acetone, filtered off and dried. Yield: 0.045 g (45%, melting point >250° C.) of Intermediate 12.

Example A8

Preparation of Intermediate 13

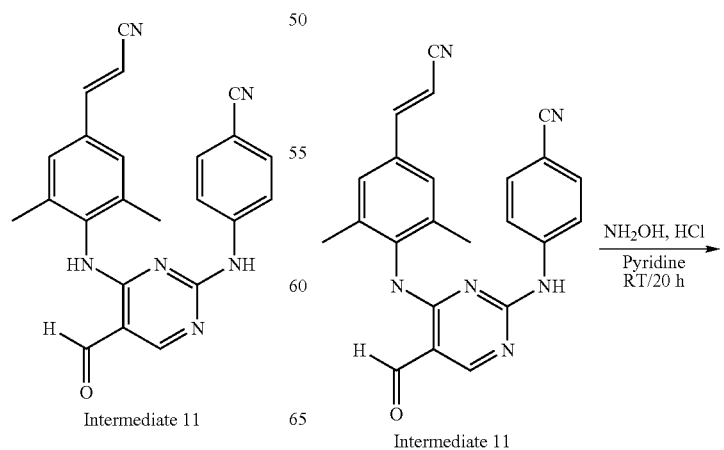

-continued

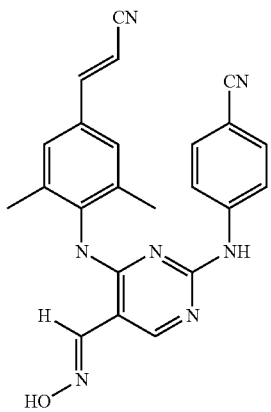

Intermediate 13

A mixture of intermediate 11 (0.000254 mol) and hydroxylamine hydrochloride (0.000380 mol) in pyridine (3 ml) was stirred at room temperature for 20 hours, then poured in water. The precipitate was filtered off, washed with water and Et$_2$O and dried. Yield: 0.048 g. of intermediate 13 (39%, melting point: >250° C.).

Example B1

Preparation of Compound 2

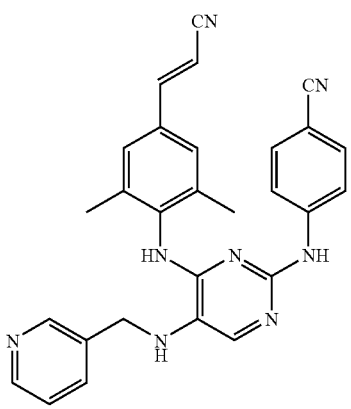

A few drops of acetic acid was added to a mixture at room temperature of cyanoborohybride on solid support (0.00042 mol), Intermediate 7 (0.00021 mol) and 3-pyridinecarboxaldehyde (0.000315 mol) in acetonitrile (5 ml). The mixture was stirred at room temperature for 40 hours and then filtered. The mixture was poured in water and K$_2$CO$_3$ 10% and extracted with CH$_2$Cl$_2$. The organic layer was dried over magnesium sulfate, filtered and the solvent evaporated. The residue was purified by column chromatography over silica gel (eluent: CH$_2$Cl$_2$/MeOH/NH$_4$OH 97/3/0.1; 10 μm). The pure fractions were collected and the solvent evaporated. Yielding: 0.041 g. This fraction was crystallized from diisopropyl-ethylether. The precipitate was filtered off and dried. Yield: 0.034 g of compound 2 (34%, melting point: 140° C.).

Second Method:

In this method, 3 equivalents of sodium cyanoborohybride instead of cyanoborohybride on solid support were used and the mixture was stirred at room temperature overnight.

Example B2

Preparation of Compound 64

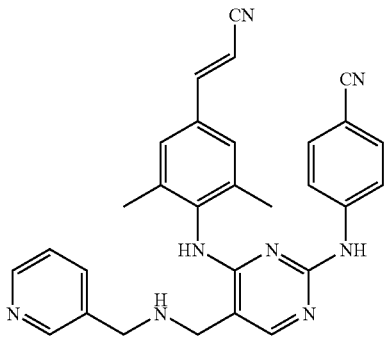

Two drops of acetic acid was added at room temperature to a mixture of sodium cyanoborohybride (0.00114 mol), intermediate 11 (0.000380 mol) and 3-(aminomethyl)-pyridine (0.000570 mol) in THF (5 ml). The mixture was stirred at room temperature for 20 hours. The mixture was poured in water and K$_2$CO$_3$ 10% and extracted with CH$_2$Cl$_2$. The organic layer was dried over magnesium sulfate, filtered and the solvent evaporated. The residue was purified by column chromatography over silica gel (eluent: CH$_2$Cl$_2$ 100; Kromasil 5 μm). The pure fractions were collected and the solvent evaporated. Yield: 0.066 g of compound 64 (36%, melting point: 236° C.).

Example B3

Preparation of Compound 72

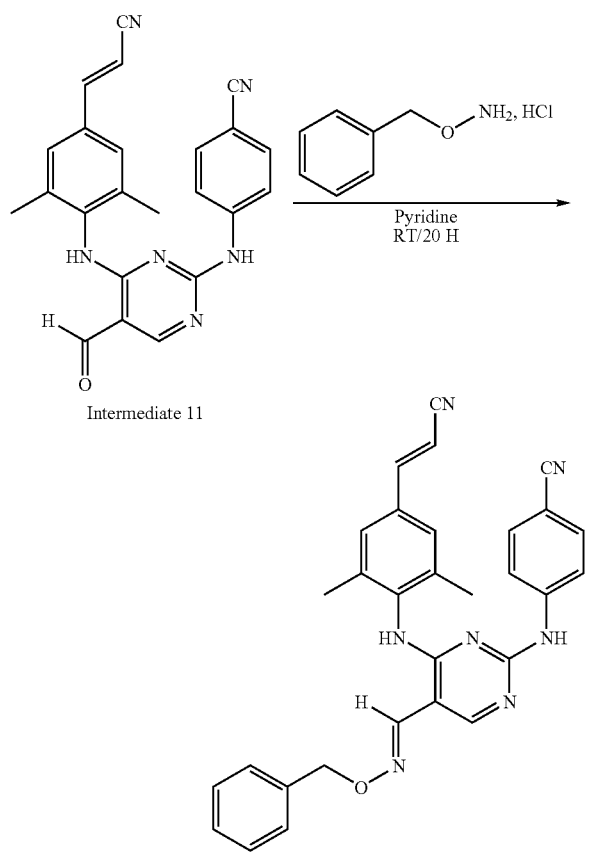

Intermediate 11

Compound 72

A mixture of intermediate 11 (0.000254 mol) and o-benzylhydroxylamine hydrochloride (0.000380 mol) in pyridine (3 ml) was stirred at room temperature for 20 hours, then poured in water. The precipitate was filtered off, washed with water and Et$_2$O and dried. Yield: 0.082 g. of Compound 72 (65%, melting point: 99° C.).

Example B4

Preparation of Compound 75

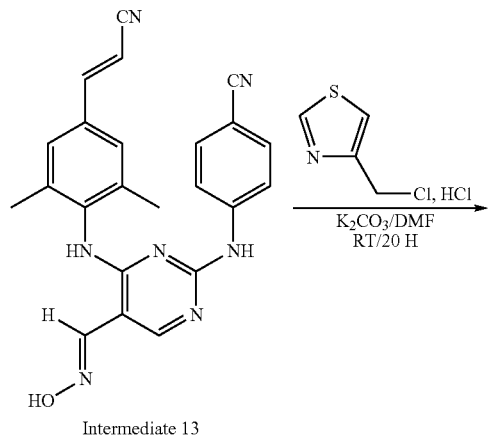

Intermediate 13

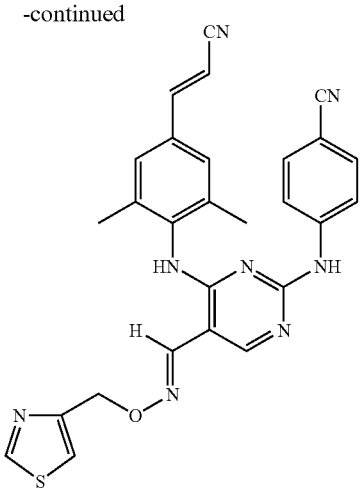

A mixture of intermediate 13 (0.000244 mol), 4-chloromethylthiazole hydrochloride (0.000269 mol) and potassium carbonate (0.000488 mol) in DMF (3 ml) was stirred at room temperature for 20 hours, and then poured in water. The precipitate was filtered off, washed with water and Et$_2$O and dried. The residue was purified by column chromatography over silica gel (eluent: CH$_2$Cl$_2$ 100 to CH$_2$Cl$_2$/MeOH 98/2; Kromasil 5 µm). The pure fractions were collected and the solvent evaporated. Yield: 0.051 g of compound 75 (41%, melting point: >250° C.).

Example B5

Preparation of Compound 82

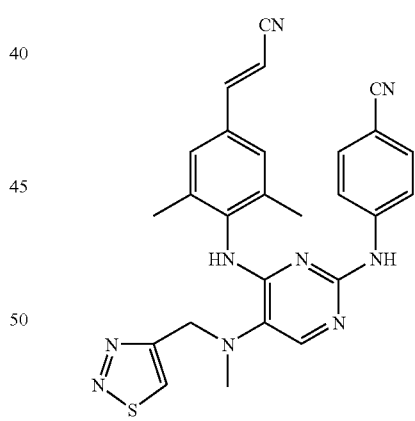

Sodium cyanoborohybride (0.00050 mol) was added at room temperature to a mixture of Compound 1 (0.000167 mol) and paraformaldehyde (0.000500 mol) in acetonitrile (10 ml). Few drops of acetic acid were added and the mixture was stirred at room temperature overnight. The mixture was poured in water and K$_2$CO$_3$ 10% and extracted with CH$_2$Cl$_2$. The organic layer was dried over magnesium sulfate, filtered and the solvent evaporated. The residue was purified by column chromatography over silica gel (eluent: CH$_2$Cl$_2$ 100 to CH$_2$Cl$_2$/MeOH 95/5; Kromasil 5 µm). The pure fractions were collected and the solvent evaporated. Yield: 0.028 g of compound 82 (34%, melting point: 216° C.).

Example B6

Preparation of Compound 84

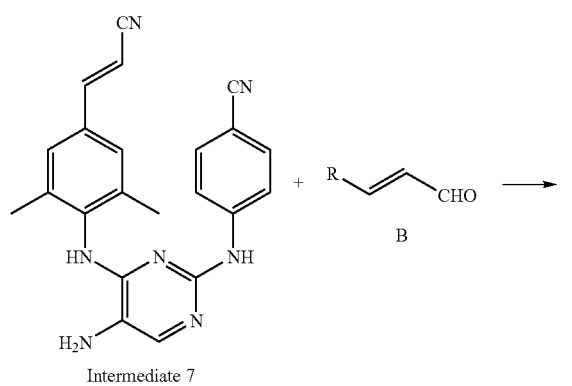

Intermediate 7

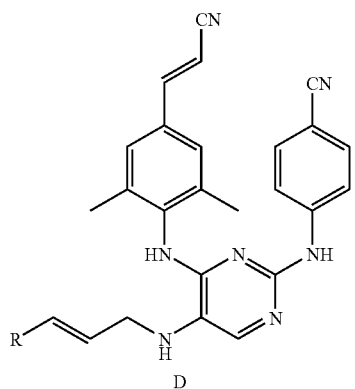

D

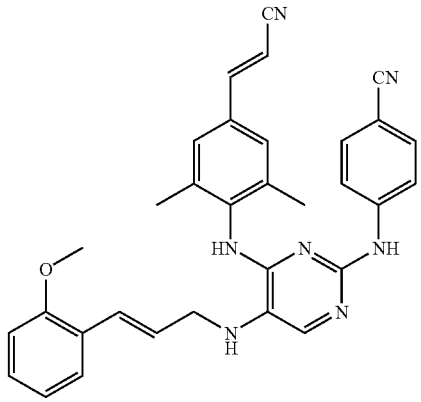

compound 84

A few drops of acetic acid was added to a mixture at room temperature of sodium cyanoborohybride (0.00119 mol), intermediate 7 (0.000393 mol) and 2-methoxycinnamaldehyde (0.000413 mol) in acetonitrile (8 ml). The mixture was stirred at room temperature for 40 hours. The mixture was poured in water and $K_2CO_3$ 10% and extracted with $CH_2Cl_2$. The organic layer was dried over magnesium sulfate, filtered and the solvent evaporated. The residue was purified by column chromatography over silica gel (eluent: $CH_2Cl_2$/AcOEt 95/5; Kromasil 5 μm). The pure fractions were collected and the solvent evaporated. Yielding: 0.010 g of compound 84 (5%, melting point: 118° C.).

Tables 1-6 list compounds that were or can be prepared according to the above Examples (Ex. No.).

TABLE 1

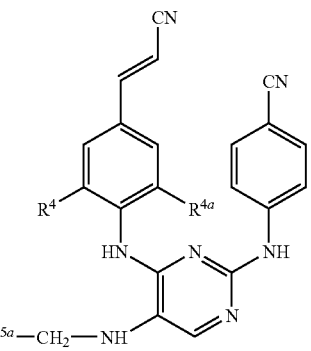

| Co. nr | Example | $R^4$ | $R^{4a}$ | $R^{5a}$ | Phys. Data and stereo-chemistry |
|---|---|---|---|---|---|
| 1 | B1 | CH₃ | CH₃ | thiadiazolyl | (E) 228° C. |
| 2 | B1 | CH₃ | CH₃ | 3-pyridinyl | (E/Z) 96/4 140° C. |
| 3 | B1 | CH₃ | CH₃ | 2-furanyl | (E)/253° C. |
| 4 | B1 | CH₃ | CH₃ | 3-furanyl | (E) 236° C. |
| 5 | B1 | CH₃ | CH₃ | 2-methoxyphenyl | (E)/230-237° C. |

TABLE 1-continued

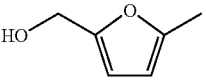

| Co. nr | Example | R⁴ | R⁴ᵃ | R⁵ᵃ | Phys. Data and stereo-chemistry |
|---|---|---|---|---|---|
| 6 | B1 | CH₃ | CH₃ | 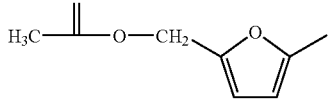 | (E) 114° C. |
| 7 | B1 | CH₃ | CH₃ | 2-pyridinyl | (E)/>250° C. |
| 8 | B1 | CH₃ | CH₃ | 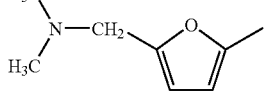 | (E) |
| 9 | B1 | CH₃ | CH₃ | 2-fluorophenyl | (E)/230° C. |
| 10 | B1 | CH₃ | CH₃ | 6-bromo-2-pyridinyl | (E)/131° C. |
| 11 | B1 | CH₃ | CH₃ | phenyl | (E)/221° C. |
| 12 | B1 | CH₃ | CH₃ | 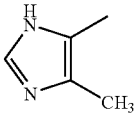 | (E) 113° C./114° C. |
| 13 | B1 | CH₃ | CH₃ | 2-thienyl | (E)/250° C. |
| 14 | B1 | CH₃ | CH₃ | 2,6-dimethoxyphenyl | (E)/227° C. |
| 15 | B1 | CH₃ | CH₃ | 3-thienyl | (E) |
| 16 | B1 | CH₃ | CH₃ | 2-chlorophenyl | (E)/221 ° C. |
| 17 | B1 | CH₃ | CH₃ | 2-methylphenyl | (E)/218° C. |
| 18 | B1 | CH₃ | CH₃ | 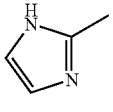 | (E) 167° C. |
| 19 | B1 | CH₃ | CH₃ | 5-chloro-2-furanyl | (E)/231° C. |
| 20 | B1 | CH₃ | CH₃ | 2-(trifluoromethyl)phenyl | (E)/231° C. |
| 21 | B1 | CH₃ | CH₃ | 5-methyl-2-thienyl | (E)/199° C. |
| 22 | B1 | CH₃ | CH₃ | 5-ethyl-2-thienyl | (E)/95° C. |
| 23 | B1 | CH₃ | CH₃ | 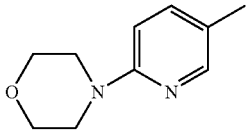 | (E/Z)97/3 >250° C. |
| 24 | B1 | CH₃ | CH₃ | 5-bromo-2-furanyl | (E) 217° C. |
| 25 | B1 | CH₃ | CH₃ | 5-methyl-2 furanyl | (E) |
| 26 | B1 | CH₃ | CH₃ | 2-phenoxy-5-pyridin-3-yl | (E)/118° C. |
| 27 | B1 | CH₃ | CH₃ | | (E) 154° C. |

TABLE 1-continued

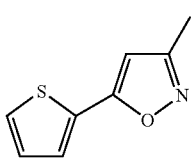

| Co. nr | Example | R⁴ | R⁴ᵃ | R⁵ᵃ | Phys. Data and stereo-chemistry |
|---|---|---|---|---|---|
| 28 | B1 | CH₃ | CH₃ | 5-[3-(trifluoromethyl)phenyl]-2-furanyl | (E)/131° C. |
| 29 | B1 | CH₃ | CH₃ | 3-(trifluoromethyl)phenyl | (E)/107° C. |
| 30 | B1 | CH₃ | CH₃ | 4-(trifluoromethyl)phenyl | (E)/114° C. |
| 31 | B1 | CH₃ | CH₃ | 5-(3-chlorophenyl)-2-furanyl | (E)/116° C. |
| 32 | B1 | CH₃ | CH₃ | 4-chlorophenyl | (E)/130° C. |
| 33 | B1 | CH₃ | CH₃ | 5-phenyl-2-furanyl | (E)/112° C. |
| 34 | B1 | CH₃ | CH₃ | 4-(phenylmethoxy)phenyl | (E)/104° C. |
| 35 | B1 | CH₃ | CH₃ | 5-(4-bromophenyl)-2-furanyl | (E)/118° C. |
| 36 | B1 | CH₃ | CH₃ | 3-(phenoxy)phenyl | (E)/170° C. |
| 37 | B1 | CH₃ | CH₃ | 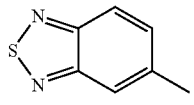 | (E)/163° C. |
| 38 | B1 | CH₃ | CH₃ | 5-(4-chlorophenyl)-2-furanyl | (E)/177° C. |
| 39 | B1 | CH₃ | CH₃ | 2-benzofuranyl | (E)/149° C. |
| 40 | B1 | CH₃ | CH₃ | 4-phenoxyphenyl | (E)/113° C. |
| 41 | B1 | CH₃ | CH₃ | 5-(2,4-dichlorophenyl)-2-furanyl | (F)/172° C. |
| 42 | B1 | CH₃ | CH₃ | 4-phenyl-2-thienyl | (E)/127° C. |
| 43 | B1 | CH₃ | CH₃ | 5-methyl-3-phenyl-4-isoxazolyl | (E)/>250° C. |
| 44 | B1 | CH₃ | CH₃ | 5-phenyl-2-thienyl | (E)/113° C. |
| 45 | B1 | CH₃ | CH₃ | 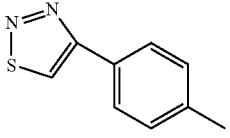 | (E)/209° C. |
| 46 | B1 | CH₃ | CH₃ | 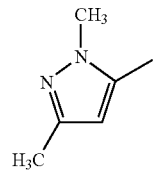 | (E)/132° C. |
| 47 | B1 | CH₃ | CH₃ | 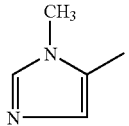 | (E)/250° C. |
| 48 | B1 | CH₃ | CH₃ |  | (E)/>250° C. |

TABLE 1-continued

[Structure: pyrimidine core with (E)-3-cyanovinyl phenyl group bearing R⁴ and R⁴ᵃ substituents connected via NH; 4-cyanophenyl-NH at 2-position; R⁵ᵃ-CH₂-NH at 5-position]

| Co. nr | Example | R⁴ | R⁴ᵃ | R⁵ᵃ | Phys. Data and stereo-chemistry |
|---|---|---|---|---|---|
| 49 | B1 | CH₃ | CH₃ | 5-methylthiazol-2-yl | (E)/109° C. |
| 50 | B1 | CH₃ | CH₃ | 2-methylthiazol-5-yl | (E)/>250° C. |
| 51 | B1 | CH₃ | CH₃ | 1,5-dimethyl-1H-pyrrol-2-yl | (E)/115° C. |
| 52 | B1 | CH₃ | CH₃ | 2,4-dimethyl-5-tert-butyl-thiazol-yl | (E)/149° C. |
| 53 | B1 | CH₃ | CH₃ | 4-methylthiazol-2-yl | (E)/>250° C. |
| 54 | B1 | CH₃ | CH₃ | 2-ethynylphenyl | (E)/224° C. |
| 55 | B1 | CH₃ | CH₃ | 2-(benzyloxy)-phenyl (with methyl) | (E)/103° C. |
| 56 | B1 | CH₃ | CH₃ | 2-ethoxyphenyl (with methyl) | (E)/125° C. |

TABLE 1-continued
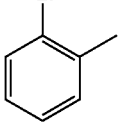
| Co. nr | Example | R⁴ | R⁴ᵃ | R⁵ᵃ | Phys. Data and stereo-chemistry |
|---|---|---|---|---|---|
| 57 | B1 | CH₃ | CH₃ | 2-Et-phenyl | (E)/228° C. |
| 58 | B1 | CH₃ | CH₃ | 2-phenyl-phenyl | (E)/233° C. |
| 59 | B1 | CH₃ | CH₃ | 2-CN-phenyl | (E)/165° C. |
TABLE 2
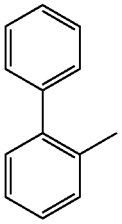
| Comp. No. | Example | R⁴ | R⁴ᵃ | R⁵ᵇ | Phys. data |
|---|---|---|---|---|---|
| 60 | B2 | CH₃ | CH₃ | 2-pyridyl | (E) 209° C. |
| 61 | B2 | CH₃ | CH₃ | 5-methyl-2-furanyl | (E) 187° C. |
| 62 | B2 | CH₃ | CH₃ | 4-pyridyl | (E) >250° C. |

TABLE 2-continued

[Structure: central pyrimidine with 2-NH linked to 4-cyanophenyl, 4-NH linked to a 2,6-disubstituted (R⁴, R⁴ᵃ) phenyl bearing a 4-(2-cyanovinyl) group, and 5-CH₂-NH-CH₂-R⁵ᵇ substituent]

R⁵ᵇ—CH₂—NH—CH₂—

| Comp. No. | Example | R⁴ | R⁴ᵃ | R⁵ᵇ | Phys. data |
|---|---|---|---|---|---|
| 63 | B2 | CH₃ | CH₃ | 2-furanyl | (E) 228° C. |
| 64 | B2 | CH₃ | CH₃ | 3-pyridyl | (E) 236° C. |
| 65 | B2 | CH₃ | CH₃ | 2-thienyl | (E) 219° C. |
| 66 | B2 | CH₃ | CH₃ | 2-pyridyl | (E/Z:98/2) 175° C. |
| 67 | B2 | CH₃ | CH₃ | phenyl | (E) 94° C. |
| 68 | B2 | CH₃ | CH₃ | 2-thienyl | (E) 205° C. |
| 69 | B2 | CH₃ | CH₃ | 4-(aminosulfonyl)phenyl | (E/Z:90/10) 206° C. |
| 70 | B2 | CH₃ | CH₃ | benzyl | (E/Z:96/4) 150° C. |

TABLE 3

| Comp. nr | Example | R⁵ᶜ | Phys. Data and stereochemistry |
|---|---|---|---|
| 71 | B3 | phenyl | (E) 167° C. |
| 72 | B3 | benzyl | (E) 99° C. |
| 73 | B4 | pyridin-2-ylmethyl | (E) 232° C. |
| 74 | B4 | (3,5-dimethylisoxazol-4-yl)(3-ethyl-1,2,4-oxadiazol-5-yl) | (E) >250° C. |
| 75 | B4 | thiazol-4-ylmethyl | (E) >250° C. |
| 76 | B4 | (2-methylthiazol-4-yl)methyl | (E) >250° C. |
| 77 | B4 | (5-methyl-3-ethylisoxazol-? ) | (E) 118° C. |
| 78 | B4 | 5-(3-trifluoromethylphenyl)-3-ethylisoxazol | (E) 150° C. |

TABLE 3-continued
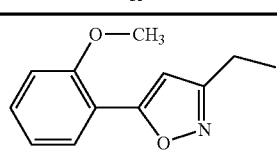
| Comp. nr | Example | R$^{5c}$ | Phys. Data and stereo-chemistry |
|---|---|---|---|
| 79 | B4 | 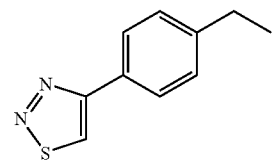 | (E) 242° C. |
| 80 | B4 | 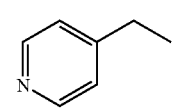 | (E) 239° C. |
| 81 | B4 | 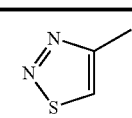 | (E) >250° C. |
TABLE 4
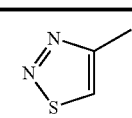
| Comp. nr | Example | R$^{5e}$ | Phys. Data and stereo-chemistry |
|---|---|---|---|
| 82 | B5 | 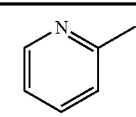 | (E) 216° C. |
TABLE 4-continued
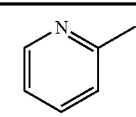
| Comp. nr | Example | R$^{5e}$ | Phys. Data and stereo-chemistry |
|---|---|---|---|
| 83 | B5 | 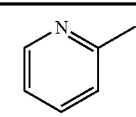 | (E) 223° C. |

TABLE 5

[Structure: pyrimidine core with 2-NH to 4-cyanophenyl, 4-NH to phenyl bearing R4, R4a and CH=CH-CN (acrylonitrile), and 5-position with R5e—CH=CH—CH2—NH—]

| Comp. nr | Example | R5e | Phys. Data and stereochemistry |
|---|---|---|---|
| 84 | B6 | 2-methoxyphenyl (OMe) | (E/E) 118° C. |
| 85 | B6 | 2-methylphenyl | (E/E) 116° C. |
| 86 | B6 | furan-2-yl | (E/E) 116° C. |
| 87 | B6 | 3-methylfuran-2-yl | (E/E) 130° C. |
| 88 | B6 | thiophen-2-yl | (E/E) 140° C. |

TABLE 6

[Structure: pyrimidine core with 2-NH to 4-cyanophenyl, 4-NH to phenyl bearing R4, R4a and CH=CH-CN, and 5-position with R5f—NH—CH2—]

| Comp. nr | Example | R4 | R4a | R5f | Phys. Data and stereo-chemistry |
|---|---|---|---|---|---|
| 89 | B2 | CH3 | CH3 | phenyl | (E) 123° C. |

Formulation Examples

Capsules

A compound of formula (I) is dissolved in organic solvent such as ethanol, methanol or methylene chloride, preferably, a mixture of ethanol and methylene chloride. Polymers such as polyvinylpyrrolidone copolymer with vinyl acetate (PVP-VA) or hydroxypropylmethylcellulose (HPMC), typically 5 mPa.s, are dissolved in organic solvents such as ethanol, methanol methylene chloride. Suitably the polymer is dissolved in ethanol. The polymer and compound solutions are mixed and subsequently spray dried. The ratio of compound/polymer is selected from 1/1 to 1/6. Intermediate ranges can be 1/1.5 and 1/3. A suitable ratio can be 1/6. The spray-dried powder, a solid dispersion, is subsequently filled in capsules for administration. The drug load in one capsule ranges between 50 and 100 mg depending on the capsule size used.

Film-Coated Tablets

Preparation of Tablet Core

A mixture of 100 g of a compound of formula (I), 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there is added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methylcellulose in 75 ml of denaturated ethanol there is added a solution of 5 g of ethylcellulose in 150 ml of dichloromethane. Then there is added 75 ml of dichloromethane and 2.5 ml 1,2,3-propanetriol. 10 g of polyethylene glycol is molten and dissolved in 75 ml of dichloromethane. The latter solution is added to the former and then there is added 2.5 g of magnesium octadecanoate, 5 g of polyvinylpyrrolidone and 30 ml of concentrated color suspension and the whole is homogenized. The tablet cores are coated with the thus obtained mixture in a coating apparatus.

Antiviral Spectrum:

Because of the increasing emergence of drug resistant HIV strains, the present compounds were tested for their potency against clinically isolated HIV strains harboring several mutations. These mutations are associated with resistance to reverse transcriptase inhibitors and result in viruses that show various degrees of phenotypic cross-resistance to the currently commercially available drugs such as for instance AZT and delavirdine.

The antiviral activity of the compound of the present invention has been evaluated in the presence of wild type HIV and HIV mutants bearing mutations at the reverse transcriptase gene. The activity of the compounds is evaluated using a cellular assay and the residual activity is expressed in $pEC_{50}$ values. The columns IIIB and A-G in the table list the $pEC_{50}$ values against various strains IIIB, A-G.

Strain IIIB is wild type HIV-LAI strain

Strain A contains mutation Y181C in HIV reverse transcriptase,

Strain B contains mutation K103N in HIV reverse transcriptase,

Strain C contains mutation L100I in HIV reverse transcriptase,

Strain D contains mutation Y188L in HIV reverse transcriptase,

Strain E contains mutations L100I and K103N in HIV reverse transcriptase,
Strain F contains mutations K103N and Y181C in HIV reverse transcriptase, and

Strain G contains mutations L100I, K103N, Y181C, V179I, Y181C, E138G, V179I, L2214F, V278V/I and A327A/V in HIV reverse transcriptase.

| Compound number | IIIB | A | B | C | D | E | F | G |
|---|---|---|---|---|---|---|---|---|
| 1 | 8.9 | 8.3 | 9 | 8.7 | 8.1 | 8.2 | 8.6 | 6.8 |
| 3 | 7.8 | 8 | 8.1 | 8.1 | 7.9 | 7.5 | 7.4 | 5 |

The invention claimed is:

1. A compound of formula (I''')

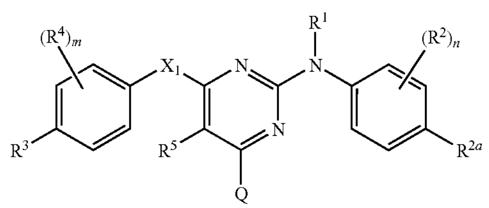

a N-oxide, a pharmaceutically acceptable addition salt, or a stereochemically isomeric form thereof, wherein n is 0, 1, 2, 3;

m is 0, 1, 2, 3;

each $R^1$ independently is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, or with $C_{1-6}$alkylcarbonyloxy;

each $R^2$ independently is hydroxy; halo; $C_{1-6}$alkyl; $C_{1-6}$alkyloxycarbonyl;

$R^{2a}$ is cyano; aminocarbonyl; amino; $C_{1-6}$alkyl; halo; $C_{1-6}$alkyloxy $X_1$ is —$NR^1$—, —O—, —C(═O)—, —$CH_2$—, —CHOH—, —S—, —S(═O)r;

$R^3$ is $C_{1-6}$alkyl substituted with cyano $R^4$ is halo; hydroxy; $C_{1-6}$alkyl; $C_{1-6}$alkyloxy; cyano; nitro; polyhalo$C_{1-6}$alkyl; $C_{1-6}$alkyloxycarbonyl; amino; mono- or di($C_{1-4}$alkyl)amino;

$R^5$ is a radical of formula —Y-Alk-L, -Alk'-Y-L or -Alk'-Y-Alk-L;

each Alk or Alk' independently is a bivalent $C_{1-6}$alkyl or $C_{2-6}$alkenyl group;

L is aryl or Het;

Y is O, S, —$S(═O)_r$—, $NR^1$; —CH═N—O—;

Het is a 5- or 6-membered completely unsaturated ring system wherein one, two, three or four ring members are hetero atoms each independently selected from the group consisting of nitrogen, oxygen and sulfur, and wherein the remaining ring members are carbon atoms; and, where possible, any nitrogen ring member may optionally be substituted with $C_{1-6}$alkyl; which ring system may optionally be annelated with a benzene ring; and wherein any ring carbon atom, including any carbon of an optionally annelated benzene ring, may, each independently, optionally be substituted with a substituent selected from halo, hydroxy, mercapto, cyano, $C_{1-6}$alkyl, hydroxy$C_{1-4}$alkyl, carboxy$C_{1-4}$alkyl, $C_{1-4}$alkyloxy$C_{1-4}$alkyl, $C_{1-4}$alkyloxycarbonyl$C_{1-4}$alkyl, cyano$C_{1-4}$alkyl, mono- and di($C_{1-4}$alkyl)amino$C_{1-4}$ alkyl, $Het^1C_{1-4}$alkyl, aryl$C_{1-4}$alkyl, polyhalo$C_{1-4}$alkyl, $C_{3-7}$cycloalkyl, $C_{2-6}$alkenyl, aryl-$C_{2-4}$alkenyl, $C_{1-4}$alkyloxy, —$OCONH_2$, polyhalo$C_{1-4}$alkyloxy, aryloxy, amino, mono- and di-$C_{1-4}$alkylamino, pyrrolidinyl, piperidinyl, morpholinyl, piperazinyl, 4-$C_{1-6}$alkylpiperazinyl, $C_{1-4}$alkylcarbonylamino, formyl, $C_{1-4}$alkylcarbonyl, $C_{1-4}$alkyloxy-carbonyl, aminocarbonyl, mono- and di$C_{1-4}$alkylaminocarbonyl, aryl, $Het^1$;

$Het^1$ is pyridyl, thienyl, furanyl, oxazolyl, isoxazolyl, imidazolyl, pyrazolyl, thiazolyl, thiadiazolyl, oxadiazolyl quinolinyl, benzothienyl, benzofuranyl; which each may optionally be substituted with one or two $C_{1-4}$alkyl radicals;

Q is hydrogen, $C_{1-6}$alkyl, halo, polyhalo$C_{1-6}$alkyl, or —$NR^9R^{10}$;

$R^9$ and $R^{10}$ each independently are hydrogen; $C_{1-6}$alkyl each aryl is phenyl or phenyl substituted with one, two, three, four or five substituents each independently selected from halo, hydroxy, mercapto, $C_{1-6}$alkyl, $C_{2-6}$alkenyl, $C_{2-6}$alkynyl, hydroxy$C_{1-6}$alkyl, amino$C_{1-6}$ alkyl, mono or di($C_{1-6}$alkyl)amino$C_{1-6}$alkyl, $C_{1-6}$alkylcarbonyl, $C_{3-7}$cycloalkyl, $C_{1-6}$alkyloxy, phenyl$C_{1-6}$ alkyloxy, $C_{1-6}$alkyloxycarbonyl, aminosulfonyl, $C_{1-6}$alkylthio, cyano, nitro, polyhalo$C_{1-6}$alkyl, polyhalo$C_{1-6}$alkyloxy, aminocarbonyl, phenyl, $Het^1$.

2. A compound according to claim 1 wherein Het is a heterocycle selected from pyrrolyl, furanyl, thienyl, pyrazolyl, imidazolyl, oxazolyl, isoxazolyl, thiazolyl, isothiazolyl, triazolyl, tetrazolyl, thiatriazolyl, thiadiazolyl oxadiazolyl, pyridyl, pyrimidinyl, pyrazinyl, pyridazinyl, benzofuranyl, benzothienyl, benzimidazolyl, benzoxazolyl, benzothiazolyl, benzotriazolyl, indolyl, benzothiadiazolyl, benzofurazanyl, benzoxadiazolyl, indazolyl, quinolinyl, said heterocycle optionally being substituted on its carbon atoms with one, two or three substituents each independently selected from halo, hydroxy, mercapto, cyano, $C_{1-6}$alkyl, hydroxy$C_{1-4}$alkyl, carboxy$C_{1-4}$alkyl, $C_{1-4}$alkyloxy$C_{1-4}$alkyl, $C_{1-4}$alkyloxycarbonyl-$C_{1-4}$alkyl, cyano$C_{1-4}$alkyl, mono- and di($C_{1-4}$alkyl)amino$C_{1-4}$alkyl, Het $C_{1-4}$alkyl, aryl$C_{1-4}$alkyl, polyhalo$C_{1-4}$alkyl, $C_{3-7}$cycloalkyl, aryl$C_{2-4}$alkenyl, $C_{1-4}$alkyloxy, —$OCONH_2$, polyhalo$C_{1-4}$alkyloxy, aryloxy, amino, mono- and di-$C_{1-4}$alkylamino, pyrrolidinyl, piperidinyl, morpholinyl, piperazinyl, 4-$C_{1-6}$alkylpiperazinyl, $C_{1-4}$alkylcarbonylamino, formyl, $C_{1-4}$alkylcarbonyl, aryl, $C_{1-4}$alkyloxycarbonyl, aminocarbonyl, mono- and di$C_{1-4}$ alkylaminocarbonyl, $Het^1$.

3. A compound according to claim 1 wherein Het is a heterocycle selected from pyrrolyl, furanyl, thienyl, pyrazolyl, imidazolyl, oxazolyl, isoxazolyl, thiazolyl, isothiazolyl, triazolyl, tetrazolyl, thiatriazolyl, to thiadiazolyl oxadiazolyl, pyridyl, pyrimidinyl, pyrazinyl, pyridazinyl, benzofuranyl, indolyl, benzothiadiazolyl, quinolinyl, said heterocycle optionally being substituted on its carbon atoms with one, two or three substituents each independently selected from halo, hydroxy, cyano, $C_{1-6}$alkyl, $C_{1-4}$alkyloxycarbonyl-$C_{1-4}$alkyl, amino, mono- and di-$C_{1-4}$alkylamino, morpholinyl, $C_{1-4}$alkylcarbonylamino, aminocarbonyl, mono- and di$C_{1-4}$alkylaminocarbonyl, aryl, $Het^1$.

4. A compound according to claim 1 wherein Het is a heterocycle selected from pyrrolyl, furanyl, thienyl, oxadiazolyl, pyridyl, said heterocycle optionally being substituted on its carbon atoms with one, two or three substituents each independently selected from halo, hydroxy, $C_{1-6}$alkyl, phenyl, $Het^1$ (the latter in particular being pyridyl).

5. A compound according to claim 1 wherein n is 0, 1 or 2;

m is 0, 1 or 2;
$R^1$ is hydrogen; or $C_{1-6}$alkyl;
$R^2$ is hydroxy; halo; $C_{1-6}$alkyl cyano; nitro; amino; mono- or di($C_{1-6}$alkyl)amino; trifluoromethyl;
$R^{2a}$ is cyano; aminocarbonyl; amino; $C_{1-6}$alkyl; halo; $C_{1-6}$alkyloxy
$X_1$ is —$NR^1$—, —O—, —S—, —S(=O)r—;
$R^3$ is $C_{2-6}$alkenyl substituted with cyano;
$R^4$ is halo; hydroxy; $C_{1-6}$alkyl $C_{1-6}$alkyloxy; cyano; trifluoromethyl;
Q is hydrogen or —$NR^9R^{10}$.

6. A compound according to claim 5 wherein
$R^2$ is halo, $C_{1-6}$alkyl
$R^{2a}$ is halo, cyano, aminocarbonyl, $C_{1-6}$alkyl optionally substituted with cyano or aminocarbonyl, $C_{2-6}$alkenyl;
$X_1$ is —NH—, —N(CH$_3$)—, —O—, —S—;
$R^4$ is halo, $C_{1-4}$alkyl, $C_{1-4}$alkyloxy, or cyano;
Y is O, $NR^1$; —CH=N—O—;
Q is hydrogen, amino, mono- or di-$C_{1-4}$alkylamino.

7. A compound according to claim 1 wherein the compound has the formula

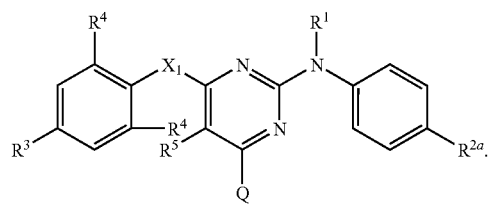

(I''')

8. A pharmaceutical composition comprising a pharmaceutically acceptable carrier and as active ingredient a therapeutically effective amount of a compound as claimed in claim 1.

9. A compound according to claim 1 wherein $R^5$ is a radical of formula —Y—$C_pH_{2p}$-L or —$C_qH_{2q}$—Y—$C_pH_{2p}$-L; wherein L is aryl or Het; and
p is 1-6;
q is 1-6.

10. A compound according to claim 9 wherein
Y is O, S, $NR^1$; —CH=N—O—;
p is 1-4;
q is 1-4.

11. A compound according to claim 10 wherein
Y is $NR^1$ or —CH=N—O—;
p is 1-2;
q is 1-2.

12. A compound according to claim 4 wherein $Het^1$ is pyridyl.

13. A compound according to claim 6 wherein
n is 0;
m is 2;
$R^4$ is halo or $C_{1-4}$alkyl;
Q is hydrogen.

14. A compound according to claim 13 wherein $R^5$ is a radical of formula —Y—$C_pH_{2p}$-L or —$C_qH_{2q}$—Y—$C_pH_{2p}$-L; wherein L is aryl or Het; and
p is 1-6;
q is 1-6.

15. A compound according to claim 14 wherein
Y is O, S, $NR^1$; —CH=N—O—;
p is 1-4;
q is 1-4.

16. A compound according to claim 15 wherein
Y is $NR^1$ or —CH=N—O—;
p is 1-2;
q is 1-2.

17. A compound according to claim 16 wherein Het is a heterocycle selected from pyrrolyl, furanyl, thienyl, oxadiazolyl, pyridyl, said heterocycle optionally being substituted on its carbon atoms with one, two or three substituents each independently selected from halo, hydroxy, $C_{1-6}$alkyl, phenyl, $Het^1$.

18. A compound according to claim 17 wherein $Het^1$ is pyridyl.

* * * * *